US012275786B2

(12) United States Patent
Hanada et al.

(10) Patent No.: US 12,275,786 B2
(45) Date of Patent: *Apr. 15, 2025

(54) ANTI-THYROGLOBULIN T CELL RECEPTORS

(71) Applicant: The United States of America, as represented by the Secretary, Department of Health and Human Services, Bethesda, MD (US)

(72) Inventors: Kenichi Hanada, Bethesda, MD (US); Qiong J. Wang, Highland Park, NJ (US); James C. Yang, Bethesda, MD (US); Zhiya Yu, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 314 days.

This patent is subject to a terminal disclaimer.

(21) Appl. No.: 17/817,599

(22) Filed: Aug. 4, 2022

(65) Prior Publication Data

US 2022/0389093 A1 Dec. 8, 2022

Related U.S. Application Data

(60) Continuation of application No. 16/586,310, filed on Sep. 27, 2019, now Pat. No. 11,440,956, which is a division of application No. 15/524,869, filed as application No. PCT/US2015/060282 on Nov. 12, 2015, now Pat. No. 10,450,372.

(60) Provisional application No. 62/079,713, filed on Nov. 14, 2014.

(51) Int. Cl.
| | |
|---|---|
| *C07K 16/26* | (2006.01) |
| *A61K 39/00* | (2006.01) |
| *A61P 35/00* | (2006.01) |
| *A61P 35/04* | (2006.01) |
| *C07K 14/725* | (2006.01) |
| *A61K 38/00* | (2006.01) |

(52) U.S. Cl.
CPC ...... *C07K 16/26* (2013.01); *A61K 39/001144* (2018.08); *A61P 35/00* (2018.01); *A61P 35/04* (2018.01); *C07K 14/7051* (2013.01); *A61K 38/00* (2013.01); *A61K 2039/5156* (2013.01); *C07K 2317/34* (2013.01); *C07K 2317/565* (2013.01); *C07K 2318/20* (2013.01); *C07K 2319/00* (2013.01)

(58) Field of Classification Search
CPC .............. C07K 16/26; C07K 14/7051; C07K 2318/20
USPC ..................................................... 424/134.1
See application file for complete search history.

(56) References Cited

U.S. PATENT DOCUMENTS

| 4,874,845 A | 10/1989 | Saito et al. |
|---|---|---|
| 8,034,334 B2 | 10/2011 | Dudley et al. |
| 8,383,099 B2 | 2/2013 | Dudley et al. |
| 10,450,372 B2* | 10/2019 | Hanada .................. A61P 35/04 |
| 11,440,956 B2* | 9/2022 | Hanada .................. A61P 35/04 |
| 2012/0244133 A1 | 9/2012 | Rosenberg et al. |

FOREIGN PATENT DOCUMENTS

| WO | WO 2012/166617 A2 | 12/2012 |
|---|---|---|
| WO | WO 2015/150327 A1 | 10/2015 |

OTHER PUBLICATIONS

ClinicalTrials.gov ID NCT02390739 (pp. 1-2; Aug. 8, 2024).*
Baird et al., "Gene Engineered T-cells for the Immunotherapy of Differentiated Thyroid Cancer," poster presented at the Endocrine Society 94th Annual Meeting, (Jun. 23-26, 2012).
Baird, "Gene Engineered T-cells for the Immunotherapy of Differentiated Thyroid Cancer," Thesis, Duke University School of Medicine (2012).
Beckman et al., "Antibody Constructs in Cancer Therapy," *Cancer*, 109 (2): 170-179 (2007).
Cespedes et al., "Mouse models in oncogenesis and cancer therapy," *Clin. Transl. Oncology*, 8(5): 318-329 (2006).
Cohen et al., "Enhanced antitumor activity of murine-human hybrid T-cell receptor (TCR) in human lymphocytes is associated with improved pairing and TCR/CD3 stability," *Cancer Res.*, 66(17): 8878-86 (2006).
Davies et al., "Current Thyroid Cancer Trends in the United States," *JAMA Otolaryngol Head Neck Surg.*, 140(4):317-322 (2014).
Dennis, "Off By a Whisker," *Nature*, 442: 739-741 (2006).
Dudley et al., "Generation of Tumor-Infiltrating Lymphocyte Cultures for Use in Adoptive Transfer Therapy for Melanoma Patients," *J Immunother.*, 26(4): 332-342 (2003).
Ehlers et al., "Evidence of a Combined Cytotoxic Thyroglobulin and Thyroperoxidase Epitope-Specific Cellular Immunity in Hashimoto's Thyroiditis," *J Clin Endocrinol Metab*, 97: 1347-1354 (2012).
Fujimori et al., "A Modeling Analysis of Monoclonal Antibody Percolation Through Tumors: A Binding-Site Barrier," *Journal of Nuclear Medicine*, 31(7): 1191-1198 (1990).
Huang et al., "Recombinant immunotherapeutics: current state and perspectives regarding the feasibility and market," *Appl. Microbiol. Biotechnol.*, 87: 401-410 (2010).

(Continued)

*Primary Examiner* — Lynn A Bristol
(74) *Attorney, Agent, or Firm* — Leydig, Voit & Mayer

(57) ABSTRACT

Disclosed is a synthetic T cell receptor (TCR) having antigenic specificity for an HLA-A2-restricted epitope of thyroglobulin (TG), $TG_{470-478}$. Related polypeptides and proteins, as well as related nucleic acids, recombinant expression vectors, host cells, and populations of cells are also provided. Antibodies, or an antigen binding portion thereof, and pharmaceutical compositions relating to the TCRs of the invention are also provided. Also disclosed are methods of detecting the presence of cancer in a mammal and methods of treating or preventing cancer in a mammal.

19 Claims, 3 Drawing Sheets

Specification includes a Sequence Listing.

(56) References Cited

OTHER PUBLICATIONS

International Bureau, International Search Report in International Application No. PCT/US2015/060282, mailed Nov. 21, 2016.
International Bureau, Written Opinion in International Application No. PCT/US2015/060282, mailed Nov. 21, 2016.
Jiang et al., "Variable influences of iodine on the T-cell recognition of a single thyroglobulin epitope," *Immunology*, 121: 370-376 (2007).
Kloos, "Approach to the patient with a positive serum thyroglobulin and a negative radioiodine scan after initial therapy for differentiated thyroid cancer," *J. Clin. Endocrinol. Metab.*, 93(5): 1519-1525 (2008).
Kochenderfer et al., "B-cell depletion and remissions of malignancy along with cytokine-associated toxicity in a clinical trial of anti-CD19 chimeric-antigen-receptor-transduced T cells," *Blood*, 119(12): 2709-2720 (2012).
Matsuoka et al., "Thyroglobulin-Induced Murine Thyroiditis Assessed by Intrathyroidal T Cell Receptor Sequencing," *J. Immunol.*, 152(5): 2562-68 (1994).
Nakashima et al., "The role of T cells expressing TcR V beta 13 in autoimmune thyroiditis induced by transfer of mouse thyroglobulin-activated lymphocytes: identification of two common CDR3 motifs," *Clin. Immunol. and Immunopathol.*, 80(2): 204-210 (1996).
Rao et al., "Recruitment of multiple V beta genes in the TCR repertoire against a single pathogenic thyroglobulin epitope," *Immunology*, 91: 623-27 (1997).
Riddell et al., "The use of anti-CD3 and anti-CD28 monoclonal antibodies to clone and expand human antigen-specific T cells," *Journal of Immunological Methods*, 128: 189-201 (1990).
Robbins et al., "Tumor regression in patients with metastatic synovial cell sarcoma and melanoma using genetically engineered lymphocytes reactive with NY-ESO-1," *J. Clin. Oncol.*, 29(7): 917-24 (2011).
Rudnick et al., "Affinity and Avidity in Antibody-Based Tumor Targeting," *Cancer Biother. and Radiopharma.*, 24 (2): 155-162 (2009).
Stetson et al., "Constitutive Cytokine mRNAs Mark Natural Killer (NK) and NK T Cells Poised for Rapid Effector Function," *The Journal of Experimental Medicine*, 198 (7) : 1069-76 (2003).
Talmadge et al., "Murine Models to Evaluate Novel and Conventional Therapeutic Strategies for Cancer," *Am. Journal of Pathology*, 170 (3): 793-804 (2007).
Thurber et al., "Antibody tumor penetration: Transport opposed by systemic and antigen-mediated clearance," *Adv. Drug Delivery Reviews*, 60: 1421-1434 (2008).
Topalian et al., "Tumor-specific cytolysis by lymphocytes infiltrating human melanomas," *The Journal of Immunology*, 142(10): 3714-25 (1989).
Van Staveren et al., "Human Thyroid Tumor Cell Lines Derived from Different Tumor Types Present a Common Dedifferentiated Phenotype," *Cancer Research*, 67(17): 8113-20 (2007).
Voskoglu-Nomikos et al., "Clinical Predictive Value of the in Vitro Cell Line, Human Xenograft, and Mouse Allograft Preclinical Cancer Models," *Clin. Can. Res.*, 9: 4227-4239 (2003).
Wang et al., "Development of a genetically-modified novel T-cell receptor for adoptive cell transfer against renal cell carcinoma," *J. Immunol. Methods*, 366(1-2): 43-51 (2011).
Zhao et al., "Primary Human Lymphocytes Transduced with NY-ESO-1 Antigen-Specific TCR Genes Recognize and Kill Diverse Human Tumor Cell Lines," *J. Immunol.*, 174(7): 4415-23 (2005).
U.S. Appl. No. 16/586,310, filed Sep. 27, 2019.
U.S. Appl. No. 15/524,869, filed May 5, 2017.

* cited by examiner

ANTI-THYROGLOBULIN T CELL RECEPTORS

CROSS-REFERENCE TO RELATED APPLICATIONS

This patent application is a continuation application of U.S. patent application Ser. No. 16/586,310, filed Sep. 27, 2019, now U.S. Pat. No. 11,440,956, which is a divisional application of U.S. patent application Ser. No. 15/524,869, filed May 5, 2017, now U.S. Pat. No. 10,450,372, which is a U.S. national stage of PCT/US2015/060282, filed Nov. 12, 2015, which claims the benefit of U.S. Provisional Patent Application No. 62/079,713, filed Nov. 14, 2014, each of which is incorporated by reference herein in its entirety.

STATEMENT REGARDING FEDERALLY SPONSORED RESEARCH OR DEVELOPMENT

This invention was made with Government support under project number Z01 BC010937 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 72,652 byte Byte ASCII (Text) file named "764464.xml," dated Aug. 2, 2022.

BACKGROUND OF THE INVENTION

The incidence of thyroid cancer in the United States has been increasing over the last four decades (Davies et al., *JAMA Otolaryngol Head Neck Surg.*, 140(4): 317-322 (2014)). Despite advances in treatments such as thyroidectomy and adjuvant radioactive iodine (RAI) therapy, the prognosis for thyroid cancer, particularly advanced or metastatic thyroid cancer, may be poor. Accordingly, there exists an unmet need for additional treatments for cancer, particularly thyroid cancer.

BRIEF SUMMARY OF THE INVENTION

An embodiment of the invention provides an isolated or purified T cell receptor (TCR) having antigenic specificity for human thyroglobulin (TG) and comprising an alpha (α) chain complementarity determining region (CDR) 1 comprising the amino acid sequence of SEQ ID NO: 3, an α chain CDR2 comprising the amino acid sequence of SEQ ID NO: 4, an α chain CDR3 comprising the amino acid sequence of SEQ ID NO: 5, a beta (β) chain CDR1 comprising the amino acid sequence of SEQ ID NO: 6, a β chain CDR2 comprising the amino acid sequence of SEQ ID NO: 7, and a β chain CDR3 comprising the amino acid sequence of SEQ ID NO: 8.

An embodiment of the invention provides an isolated or purified TCR having antigenic specificity for human TG and comprising an α chain CDR1 comprising the amino acid sequence of SEQ ID NO: 44, an α chain CDR2 comprising the amino acid sequence of SEQ ID NO: 45, an α chain CDR3 comprising the amino acid sequence of SEQ ID NO: 46, a β chain CDR1 comprising the amino acid sequence of SEQ ID NO: 47, a β chain CDR2 comprising the amino acid sequence of SEQ ID NO: 48, and a β chain CDR3 comprising the amino acid sequence of SEQ ID NO: 49.

The invention further provides related polypeptides and proteins, as well as related nucleic acids, recombinant expression vectors, host cells, and populations of cells. Further provided by the invention are antibodies, or antigen binding portions thereof, and pharmaceutical compositions relating to the TCRs (including functional portions and functional variants thereof) of the invention.

Methods of detecting the presence of cancer in a mammal and methods of treating or preventing cancer in a mammal are further provided by the invention.

DETAILED DESCRIPTION OF THE INVENTION

Figure 1A:
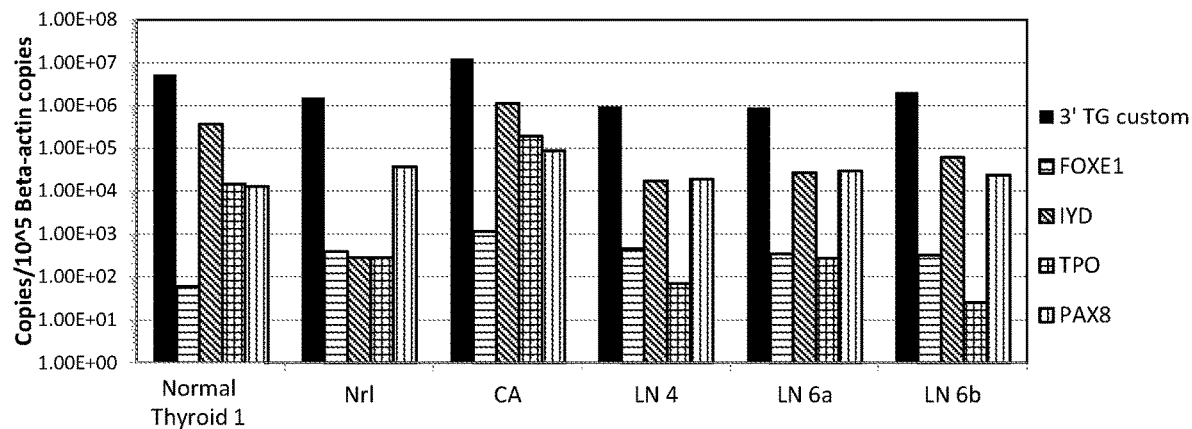
FIG. 1A is a graph showing the number of copies of TG (black bars), forkhead box E1 (FOXE1) (horizontally striped bars), iodotyrosine deiodinase (IYD) (slashed bars), thyroid peroxidase (TPO) (boxed bars), and pair box 8 (PAX8) (vertically striped bars) RNA relative to $1 \times 10^5$ ($10^5$) copies of R-actin RNA measured in two normal thyroid samples (normal thyroid 1 and 2), one primary thyroid cancer sample, and three lymph node metastasis samples (lymph node metastasis 1, 2, and 3).

An embodiment of the invention provides an isolated or purified TCR having antigenic specificity for human TG. The inventive TCR (including functional portions and functional variants thereof) may have antigenic specificity for any human TG protein, polypeptide or peptide. In an embodiment of the invention, the TCR (including functional portions and functional variants thereof) has antigenic specificity for a human TG protein comprising or consisting of the amino acid sequence of SEQ ID NO: 1. In an embodiment of the invention, the TCR (including functional portions and functional variants thereof) has antigenic specificity for a human $TG_{470-478}$ peptide comprising or consisting of the amino acid sequence of NLFGGKFLV (SEQ ID NO: 2) or a human $TG_{3-11}$ peptide comprising or consisting of the amino acid sequence of LVLEIFTLL (SEQ ID NO: 58). In a preferred embodiment of the invention, the TCR (including functional portions and functional variants thereof) has antigenic specificity for a human $TG_{470-478}$ peptide comprising or consisting of the amino acid sequence of NLFGGKFLV (SEQ ID NO: 2).

In an embodiment of the invention, the inventive TCRs (including functional portions and functional variants thereof) are able to recognize human TG in a major histocompatibility complex (MHC) class I-dependent manner. "MHC class I-dependent manner," as used herein, means that the TCR (including functional portions and functional variants thereof) elicits an immune response upon binding to TG within the context of an MHC class I molecule. The MHC class I molecule can be any MHC class I molecule known in the art, e.g., HLA-A molecules. In a preferred embodiment of the invention, the MHC class I molecule is an HLA-A2 molecule.

The TCRs (including functional portions and functional variants thereof) of the invention provide many advantages, including when expressed by cells used for adoptive cell transfer. TG has a high level of expression that is limited to differentiated thyroid cancer and normal thyroid, a dispensable tissue that may have already been removed in thyroid cancer patients. TG is also expressed in neuroblastoma. Without being bound to a particular theory or mechanism, it is believed that the inventive TCRs (including functional portions and functional variants thereof) advantageously target the destruction of cancer cells while minimizing or eliminating the destruction of normal, non-cancerous, non-thyroid cells, thereby reducing, for example, by minimizing or eliminating, toxicity. Moreover, the inventive TCRs (including functional portions and functional variants thereof) may, advantageously, successfully treat or prevent TG-positive cancers that do not respond to other types of treatment such as, for example, chemotherapy, surgery, or radiation. Additionally, the inventive TCRs (including functional portions and functional variants thereof) provide highly avid recognition of TG, which may, advantageously, provide the ability to recognize unmanipulated tumor cells (e.g., tumor cells that have not been treated with interferon (IFN)-γ, transfected with a vector encoding one or both of TG and HLA-A2, pulsed with the $TG_{470-478}$ peptide, or a combination thereof).

The phrase "antigenic specificity," as used herein, means that the TCR (including functional portions and functional variants thereof) can specifically bind to and immunologically recognize TG with high avidity. For example, a TCR (including functional portions and functional variants thereof) may be considered to have "antigenic specificity" for TG if T cells expressing the TCR (or functional portion or functional variant thereof) secrete at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, 20,000 pg/mL or more, or a range defined by any two of the foregoing values) of IFN-γ upon co-culture with (a) antigen-negative HLA-A2$^+$ target cells pulsed with a low concentration of TG peptide (e.g., about 0.05 ng/mL to about 5 ng/mL, 0.05 ng/mL, 0.1 ng/mL, 0.5 ng/mL, 1 ng/mL, 5 ng/mL, or a range defined by any two of the foregoing values) or (b) HLA-A2$^+$ target cells into which a nucleotide sequence encoding TG has been introduced such that the target cell expresses TG. Cells expressing the inventive TCRs (including functional portions and functional variants thereof) may also secrete IFN-γ upon co-culture with antigen-negative HLA-A2$^+$ target cells pulsed with higher concentrations of TG peptide.

Alternatively or additionally, a TCR (including functional portions and functional variants thereof) may be considered to have "antigenic specificity" for TG if T cells expressing the TCR (or functional portion or functional variant thereof) secrete at least twice as much IFN-γ upon co-culture with (a) antigen-negative HLA-A2$^+$ target cells pulsed with a low concentration of TG peptide or (b) HLA-A2$^+$ target cells into which a nucleotide sequence encoding TG has been introduced such that the target cell expresses TG as compared to the amount of IFN-γ expressed by a negative control. The negative control may be, for example, (i) T cells expressing the TCR (or a functional portion or functional variant thereof), co-cultured with (a) antigen-negative HLA-A2$^+$ target cells pulsed with the same concentration of an irrelevant peptide (e.g., some other peptide with a different sequence from the TG peptide) or (b) HLA-A2$^+$ target cells into which a nucleotide sequence encoding an irrelevant peptide has been introduced such that the target cell expresses the irrelevant peptide, or (ii) untransduced T cells (e.g., derived from PBMC, which do not express the TCR, or a functional portion or functional variant thereof) co-cultured with (a) antigen-negative HLA-A2$^+$ target cells pulsed with the same concentration of TG peptide or (b) HLA-A2$^+$ target cells into which a nucleotide sequence encoding TG has been introduced such that the target cell expresses TG. IFN-γ secretion may be measured by methods known in the art such as, for example, enzyme-linked immunosorbent assay (ELISA).

Alternatively or additionally, a TCR (including functional portions and functional variants thereof), may be considered to have "antigenic specificity" for TG if at least twice as many of the numbers of T cells expressing the TCR (or the functional portion or functional variant thereof), secrete IFN-γ upon co-culture with (a) antigen-negative HLA-A2$^+$ target cells pulsed with a low concentration of TG peptide or (b) HLA-A2$^+$ target cells into which a nucleotide sequence encoding TG has been introduced such that the target cell expresses TG as compared to the numbers of negative control T cells that secrete IFN-γ. The concentration of peptide and the negative control may be as described herein with respect to other aspects of the invention. The numbers of cells secreting IFN-γ may be measured by methods known in the art such as, for example, ELISPOT.

The invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for TG.

In an embodiment of the invention, the TCR comprises two polypeptide chains, each of which comprises a variable region comprising a complementarity determining region (CDR)1, a CDR2, and a CDR3 of a TCR. In an embodiment of the invention, the TCR comprises a first polypeptide chain comprising a CDR1 comprising the amino acid sequence of SEQ ID NO: 3 or 44 (CDRT of α chain), a CDR2 comprising the amino acid sequence of SEQ ID NO: 4 or 45 (CDR2 of α chain), and a CDR3 comprising the amino acid sequence of SEQ ID NO: 5 or 46 (CDR3 of α chain), and a second polypeptide chain comprising a CDR1 comprising the amino acid sequence of SEQ ID NO: 6 or 47 (CDRT of β chain), a CDR2 comprising the amino acid sequence of SEQ ID NO: 7 or 48 (CDR2 of β chain), and a CDR3 comprising the amino acid sequence of SEQ ID NO: 8 or 49 (CDR3 of β chain). In this regard, the inventive TCR can comprise any one or more of the amino acid sequences selected from the group consisting of SEQ ID NOs: 3-8 or SEQ ID NOs: 44-49. Preferably, the TCR comprises the amino acid sequences of SEQ ID NOs: 3-5, SEQ ID NOs: 6-8, SEQ ID NOs: 44-46, or SEQ ID NOs: 47-49. In an especially preferred embodiment, the TCR comprises the amino acid sequences of all of SEQ ID NOs: 3-8 or all of SEQ ID NOs: 44-49.

In an embodiment of the invention, the TCR comprises an amino acid sequence of a variable region of a TCR comprising the CDRs set forth above. In this regard, the TCR can comprise the amino acid sequence of SEQ ID NO: 9 or 50 (variable region of α chain); SEQ ID NO: 10 or 51 (variable region of β chain); both SEQ ID NOs: 9 and 10; or both SEQ ID NOs: 50 and 51. Preferably, the inventive TCR comprises the amino acid sequences of both SEQ ID NOs: 9 and 10 or both SEQ ID NOs: 50 and 51.

In an embodiment of the invention, the TCR further comprises an amino acid sequence of a constant region of a TCR. In this regard, the TCR can comprise the amino acid sequence of SEQ ID NO: 13 or 52 (constant region of α chain), SEQ ID NO: 14 or 53 (constant region of β chain), both SEQ ID NOs: 13 and 14, or both SEQ ID NOs: 52 and 53. Preferably, the inventive TCR comprises the amino acid sequences of both SEQ ID NOs: 13 and 14 or both SEQ ID NOs: 52 and 53.

In an embodiment of the invention, the inventive TCR may comprise a combination of a variable region and a constant region. In this regard, the TCR can comprise an α chain comprising the amino acid sequences of both SEQ ID NO: 9 (variable region of α chain) and SEQ ID NO: 13 (constant region of α chain); a β chain comprising the amino acid sequences of both SEQ ID NO: 10 (variable region of β chain) and SEQ ID NO: 14 (constant region of β chain); an α chain comprising the amino acid sequences of both SEQ ID NO: 50 (variable region of α chain) and SEQ ID NO: 52 (constant region of α chain); a β chain comprising the amino acid sequences of both SEQ ID NO: 51 (variable region of β chain) and SEQ ID NO: 53 (constant region of β chain); the amino acid sequences of all of SEQ ID NOs: 9, 10, 13, and 14; or the amino acid sequences of all of SEQ ID NOs: 50-53. Preferably, the inventive TCR comprises the amino acid sequences of all of SEQ ID NOs: 9, 10, 13, and 14 or all of SEQ ID NOs: 50-53.

In an embodiment of the invention, the inventive TCR may comprise a combination of any of the CDR regions described herein and a constant region. In this regard, the TCR can comprise an α chain comprising the amino acid sequences of all of SEQ ID NOs: 3-5 and 13; a β chain comprising the amino acid sequences of all of SEQ ID NOs: 6-8 and 14; or the amino acid sequences of all of SEQ ID NOs: 3-8 and 13-14. In an embodiment of the invention, the TCR can comprise an α chain comprising the amino acid sequences of all of SEQ ID NOs: 44-46 and 52; a β chain comprising the amino acid sequences of all of SEQ ID NOs: 47-49 and 53; or the amino acid sequences of all of SEQ ID NOs: 44-49 and 52-53.

In an embodiment of the invention, the inventive TCR can comprise an α chain of a TCR and a β chain of a TCR. Each of the α chain and β chain of the inventive TCR can independently comprise any amino acid sequence. In this regard, the α chain of the inventive TCR can comprise the amino acid sequence of SEQ ID NO: 11 or 54. An α chain of this type can be paired with any β chain of a TCR. In this regard, the β chain of the inventive TCR can comprise the amino acid sequence of SEQ ID NO: 12 or 55. The inventive TCR, therefore, can comprise the amino acid sequence of SEQ ID NO: 11, SEQ ID NO: 12, SEQ ID NO: 54, SEQ ID NO: 55, both SEQ ID NOs: 11 and 12, or both SEQ ID NOs: 54 and 55. Preferably, the inventive TCR comprises the amino acid sequences of both SEQ ID NOs: 11 and 12 or both SEQ ID NOs: 54 and 55.

In an embodiment of the invention, the TCR is a murine TCR or a human TCR. As used herein, the term "murine" or "human," when referring to a TCR or any component of a TCR described herein (e.g., complementarity determining region (CDR), variable region, constant region, α chain, and/or β chain), means a TCR (or component thereof) which is derived from a mouse or a human, respectively, i.e., a TCR (or component thereof) that originated from or was, at one time, expressed by a mouse T cell or a human T cell, respectively. In an embodiment of the invention, a TCR comprising (i) all of SEQ ID NOs: 3-8; (ii) SEQ ID NOs: 9 and 10; (iii) SEQ ID NOs: 11 and 12; (iv) all of SEQ ID NOs: 3-8 and 13-14; or (v) all of SEQ ID NOs: 9, 10, 13, and 14 is a murine TCR. In an embodiment of the invention, a TCR comprising (i) all of SEQ ID NOs: 44-49; (ii) SEQ ID NOs: 50 and 51; (iii) SEQ ID NOs: 54 and 55; (iv) all of SEQ ID NOs: 44-49 and 52-53; or (v) all of SEQ ID NOs: 50-53 is a human TCR. In an embodiment of the invention, the murine TCR (including functional portions and functional variants thereof) has antigenic specificity for a human $TG_{470-478}$ peptide comprising or consisting of the amino acid sequence of NLFGGKFLV (SEQ ID NO: 2) and the human TCR has antigenic specificity for a human $TG_{3-11}$ peptide comprising or consisting of the amino acid sequence of LVLEIFTLL (SEQ ID NO: 58).

Included in the scope of the invention are functional variants of the inventive TCRs described herein. The term "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to TG for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 95%, 96%, 97%, 98%, 99% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR (or functional variant thereof), polypeptide, or protein can consist essentially of the specified amino acid sequence or sequences described herein, such that other components of the TCR (or functional variant thereof), polypeptide, or protein, e.g., other amino acids, do not materially change the biological activity of the TCR (or functional variant thereof), polypeptide, or protein. In this regard, the inventive TCR (or functional variant thereof), polypeptide, or protein can, for example, consist essentially of the amino acid sequence of SEQ ID NO: 11, SEQ ID NO: 12, SEQ ID NO: 54, SEQ ID NO: 55, both SEQ ID NOs: 11 and 12, or both SEQ ID NOs: 54 and 55. Also, for instance, the inventive TCRs (including functional variants thereof), polypeptides, or proteins can consist essentially of the amino acid sequence(s) of SEQ ID NO: 9, SEQ ID NO: 10, SEQ ID NO: 50, SEQ ID NO: 51, both SEQ ID NOs: 9 and 10, or both SEQ ID NOs: 50 and 51. Furthermore, the inventive TCRs (including functional variants thereof), polypeptides, or proteins can consist essentially of the amino acid sequence of SEQ ID NO: 3 or 44 (CDR1 of α chain), SEQ ID NO: 4 or 45 (CDR2 of α chain), SEQ ID NO: 5 or 46 (CDR3 of α chain), SEQ ID NO: 6 or 47 (CDR1 of β chain), SEQ ID NO: 7 or 48 (CDR2 of β chain), SEQ ID NO: 8 or 49 (CDR3 of β chain), or any combination thereof, e.g., SEQ ID NOs: 3-5; 6-8; 3-8; 44-46; 47-49; or 44-49.

Also provided by the invention is a polypeptide comprising a functional portion of any of the TCRs (or functional variants thereof) described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR (or functional variant thereof) of which it is a part, provided that the functional portion specifically binds to TG. The term "functional portion" when used in reference to a TCR (or functional variant thereof) refers to any part or fragment of the TCR (or functional variant thereof) of the invention, which part or fragment retains the biological activity of the TCR (or functional variant thereof) of which it is a part (the parent TCR or parent functional variant thereof). Functional portions encompass, for example, those parts of a TCR (or functional variant thereof) that retain the ability to specifically bind to TG (e.g., in an HLA-A2-dependent manner), or detect, treat, or prevent cancer, to a similar extent, the same extent, or to a higher extent, as the parent TCR (or functional variant thereof). In reference to the parent TCR (or functional variant thereof), the functional portion can comprise, for instance, about 10%, 25%, 30%, 50%, 68%, 80%, 90%, 95%, or more, of the parent TCR (or functional variant thereof).

The functional portion can comprise additional amino acids at the amino or carboxy terminus of the portion, or at both termini, which additional amino acids are not found in the amino acid sequence of the parent TCR or functional variant thereof. Desirably, the additional amino acids do not interfere with the biological function of the functional portion, e.g., specifically binding to TG; and/or having the ability to detect cancer, treat or prevent cancer, etc. More desirably, the additional amino acids enhance the biological activity, as compared to the biological activity of the parent TCR or functional variant thereof.

The polypeptide can comprise a functional portion of either or both of the α and β chains of the TCRs or functional variant thereof of the invention, such as a functional portion comprising one of more of CDR1, CDR2, and CDR3 of the variable region(s) of the α chain and/or β chain of a TCR or functional variant thereof of the invention. In an embodiment of the invention, the polypeptide can comprise a functional portion comprising the amino acid sequence of SEQ ID NO: 3 or 44 (CDR1 of α chain), 4 or 45 (CDR2 of α chain), 5 or 46 (CDR3 of α chain), 6 or 47 (CDR1 of β chain), 7 or 48 (CDR2 of β chain), 8 or 49 (CDR3 of β chain), or a combination thereof. Preferably, the inventive polypeptide comprises a functional portion comprising the amino acid sequences of SEQ ID NOs: 3-5; 6-8; 44-46; 47-49; all of SEQ ID NOs: 3-8; or all of SEQ ID NOs: 44-49. More preferably, the polypeptide comprises a functional portion comprising the amino acid sequences of all of SEQ ID NOs: 3-8 or all of SEQ ID NOs: 44-49.

In an embodiment of the invention, the inventive polypeptide can comprise, for instance, the variable region of the inventive TCR or functional variant thereof comprising a combination of the CDR regions set forth above. In this regard, the polypeptide can comprise the amino acid sequence of SEQ ID NO: 9 or 50 (variable region of α chain), SEQ ID NO: 10 or 51 (variable region of β chain), both SEQ ID NOs: 9 and 10, or both SEQ ID NOs: 50 and 51. Preferably, the polypeptide comprises the amino acid sequences of both SEQ ID NOs: 9 and 10 or both SEQ ID NOs: 50 and 51.

In an embodiment of the invention, the inventive polypeptide can further comprise the constant region of the inventive TCR or functional variant thereof set forth above. In this regard, the polypeptide can comprise the amino acid sequence of SEQ ID NO: 13 or 52 (constant region of α chain), SEQ ID NO: 14 or 53 (constant region of β chain), both SEQ ID NOs: 13 and 14; or both SEQ ID NOs: 52 and 53. Preferably, the polypeptide comprises the amino acid sequences of both SEQ ID NOs: 13 and 14 or both SEQ ID NOs: 52 and 53.

In an embodiment of the invention, the inventive polypeptide may comprise a combination of a variable region and a constant region of the inventive TCR or functional variant thereof. In this regard, the polypeptide can comprise the amino acid sequences of both SEQ ID NO: 9 (variable region of α chain) and SEQ ID NO: 13 (constant region of α chain), both SEQ ID NO: 10 (variable region of β chain) and SEQ ID NO: 14 (constant region of β chain), or all of SEQ ID NOs: 9, 10, 13, and 14. In an embodiment, the polypeptide can comprise the amino acid sequences of both SEQ ID NO: 50 (variable region of α chain) and SEQ ID NO: 52 (constant region of α chain), both SEQ ID NO: 51 (variable region of β chain) and SEQ ID NO: 53 (constant region of β chain), or all of SEQ ID NOs: 50-53. Preferably, the polypeptide comprises the amino acid sequences of all of SEQ ID NOs: 9, 10, 13, and 14 or all of SEQ ID NOs: 50-53.

In an embodiment of the invention, the inventive polypeptide may comprise a combination of any of the CDR regions described herein and a constant region of the inventive TCR or functional variant thereof. In this regard, the polypeptide can comprise the amino acid sequences of all of SEQ ID NOs: 3-5 and 13, all of SEQ ID NOs: 6-8 and 14, or all of SEQ ID NOs: 3-8 and 13-14. In an embodiment of the invention, the polypeptide can comprise the amino acid sequences of all of SEQ ID NOs: 44-46 and 52, all of SEQ ID NOs: 47-49 and 53, or all of SEQ ID NOs: 44-49 and 52-53. Preferably, the polypeptide comprises the amino acid sequences of all of SEQ ID NOs: 3-8 and 13-14 or all of SEQ ID NOs: 44-49 and 52-53.

In an embodiment of the invention, the inventive polypeptide can comprise the entire length of an α or β chain of the TCR or functional variant thereof described herein. In this regard, the inventive polypeptide can comprise the amino acid sequence of SEQ ID NO: 11, SEQ ID NO: 12, SEQ ID NO: 54, SEQ ID NO: 55, both SEQ ID NOs: 11 and 12, or both SEQ ID NO: 54 and 55. Preferably, the polypeptide comprises the amino acid sequences of both SEQ ID NOs: 11 and 12 or both SEQ ID NOs: 54 and 55.

The invention further provides a protein comprising at least one of the polypeptides described herein. By "protein" is meant a molecule comprising one or more polypeptide chains.

In an embodiment, the protein of the invention can comprise a first polypeptide chain comprising the amino acid sequences of SEQ ID NOs: 3-5 or SEQ ID NOs: 44-46 and a second polypeptide chain comprising the amino acid sequence of SEQ ID NOs: 6-8 or SEQ ID NOs: 47-49. Alternatively or additionally, the protein of the invention can comprise a first polypeptide chain comprising the amino acid sequence of SEQ ID NO: 9 or 50 and a second polypeptide chain comprising the amino acid sequence of SEQ ID NO: 10 or 51. The protein can, for example, comprise a first polypeptide chain comprising (i) the amino acid sequences of both SEQ ID NOs: 9 and 13 or all of SEQ ID NOs: 3-5 and 13 and a second polypeptide chain comprising the amino acid sequences of both SEQ ID NOs: 10 and 14 or all of SEQ ID NOs: 6-8 and 14 or (ii) the amino acid sequences of both SEQ ID NOs: 50 and 52 or all of SEQ ID NOs: 44-46 and 52 and a second polypeptide chain comprising the amino acid sequences of both SEQ ID NOs: 51 and 53 or all of SEQ ID NOs: 47-49 and 53. Alternatively or additionally, the protein of the invention can comprise a first polypeptide chain comprising the amino acid sequence of SEQ ID NO: 11 or 54 and a second polypeptide chain comprising the amino acid sequence of SEQ ID NO: 12 or 55. In this instance, the protein of the invention can be a TCR. Alternatively, if, for example, the protein comprises a single polypeptide chain comprising the amino acid sequences of both SEQ ID NOs: 11 and 12, both SEQ ID NOs: 54 and 55, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

In some embodiments of the invention, the TCRs (and functional portions and functional variants thereof), polypeptides, and proteins of the invention may be expressed as a single protein comprising a linker peptide linking the α chain and the β chain. In this regard, the TCRs (and functional variants and functional portions thereof), polypeptides, and proteins of the invention comprising both SEQ ID NOs: 11 and 12, both SEQ ID NOs: 54 and 55, both SEQ ID NO: 9 and 10, both SEQ ID NOs: 50 and 51, all of SEQ ID NOs: 3-8, all of SEQ ID NOs: 44-49, all of SEQ ID NOs: 9, 10, 13, and 14, all of SEQ ID NOs: 50-53, all of SEQ ID NOs: 3-8 and 13-14, or all of SEQ ID NOs: 44-49 and 52-53 may further comprise a linker peptide. The linker peptide may advantageously facilitate the expression of a recombinant TCR (including functional portions and functional variants thereof), polypeptide, and/or protein in a host cell. The linker peptide may comprise any suitable amino acid sequence. In an embodiment of the invention, the TCR (or functional portion or variant thereof), polypeptide, or protein comprises a self-cleaving, viral linker peptide. For example, the linker peptide may comprise SEQ ID NO: 28. Upon expression of the construct including the linker peptide by a host cell, the linker peptide may be cleaved, resulting in separated α and β chains.

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

The TCRs, polypeptides, and proteins of the invention (including functional variants thereof) can be of any length, i.e., can comprise any number of amino acids, provided that the TCRs, polypeptides, or proteins (or functional variants thereof) retain their biological activity, e.g., the ability to specifically bind to TG; detect cancer in a mammal; or treat or prevent cancer in a mammal, etc. For example, the polypeptide can be in the range of from about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention (including functional variants thereof) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention (including functional variants thereof) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention (including functional variants thereof) can be obtained by methods known in the art such as, for example, de novo synthesis. Also, polypeptides and proteins can be recombinantly produced using the nucleic acids described herein using standard recombinant methods. See, for example, Green and Sambrook, Molecular Cloning: A Laboratory Manual, 4$^{th}$ ed., Cold Spring Harbor Press, Cold Spring Harbor, NY (2012). Alternatively, the TCRs, polypeptides, and/or proteins described herein (including functional variants thereof) can be commercially synthesized by companies, such as Synpep (Dublin, CA), Peptide Technologies Corp. (Gaithersburg, MD), and Multiple Peptide Systems (San Diego, CA). In this respect, the inventive TCRs (including functional variants thereof), polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional variants thereof), nucleic acids, recombinant expression vectors, host cells, populations of host cells, or antibodies, or antigen binding portions thereof. Conjugates, as well as methods of synthesizing conjugates in general, are known in the art.

An embodiment of the invention provides a nucleic acid comprising a nucleotide sequence encoding any of the TCRs (including functional portions and functional variants thereof), polypeptides, or proteins described herein. "Nucleic acid," as used herein, includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green and Sambrook et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, CO) and Synthegen (Houston, TX).

The nucleic acid can comprise any nucleotide sequence which encodes any of the TCRs (including functional portions and functional variants thereof), polypeptides, or proteins described herein. In an embodiment of the invention, the nucleic acid may comprise the nucleotide sequence of SEQ ID NO: 22 (CDR1 of α chain); the nucleotide sequence of SEQ ID NO: 23 (CDR2 of α chain); the nucleotide sequence of SEQ ID NO: 24 (CDR3 of a chain); the nucleotide sequence of SEQ ID NO: 25 (CDR1 of β chain); the nucleotide sequence of SEQ ID NO: 26 (CDR2 of β chain); or the nucleotide sequence of SEQ ID NO: 27 (CDR3 of β chain). Preferably, the nucleic acid comprises the nucleotide sequences of all of SEQ ID NOs: 22-24; all of SEQ ID NOs: 25-27; or all of SEQ ID NOs: 22-27. In an especially preferred embodiment, the nucleic acid comprises the nucleotide sequences of all of SEQ ID NOs: 22-27. In an embodiment of the invention, the nucleic acid may comprise the nucleotide sequence of SEQ ID NO: 15 (variable region α chain); SEQ ID NO: 16 (variable region β chain); or both SEQ ID NOs: 15 and 16. Preferably, the nucleic acid comprises the nucleotide sequences of both SEQ ID NOs: 15 and 16. In another embodiment of the invention, the nucleic acid may comprise the nucleotide sequence of SEQ ID NO: 17 or 56 (full-length α chain); SEQ ID NO: 18 or 57 (full length β chain); both of SEQ ID NOs: 17 and 18, or both of SEQ ID NOs: 56 and 57. Preferably, the nucleic acid comprises the nucleotide sequences of both of SEQ ID NOs: 17 and 18 or both of SEQ ID NOs: 56 and 57.

In an embodiment of the invention, the nucleic acid further comprises a nucleotide sequence that encodes the constant region of a TCR α or β chain. In this regard, any of the nucleic acids described herein may further comprise the nucleotide sequence of SEQ ID NO: 19 (constant region of α chain); SEQ ID NO: 20 (constant region of β chain); or both SEQ ID NOs: 19 and 20. Preferably, the nucleic acid comprises the nucleotide sequence of both SEQ ID NOs: 15 and 19; both SEQ ID NOs: 16 and 20; all of SEQ ID NOs: 15-16 and 19-20; all of SEQ ID NOs: 22-24 and 19; all of SEQ ID NOs: 25-27 and 20; or all of SEQ ID NOs: 22-27 and 19-20. In an especially preferred embodiment, the nucleic acid comprises the nucleotide sequences of all of SEQ ID NOs: 15-16 and 19-20 or all of SEQ ID NOs: 22-27 and 19-20.

In an embodiment of the invention, a nucleic acid comprising the nucleotide sequences of SEQ ID NOs: 56 and 57 encodes a human TCR. In an embodiment of the invention, a nucleic acid comprising the nucleotide sequence of all of SEQ ID NOs: 22-24; all of SEQ ID NOs: 25-27; all of SEQ ID NOs: 22-27; both SEQ ID NOs: 15 and 16; both SEQ ID NOs: 17 and 18; both SEQ ID NOs: 15 and 19; both SEQ ID NOs: 16 and 20; all of SEQ ID NOs: 15-16 and 19-20; all of SEQ ID NOs: 22-24 and 19; all of SEQ ID NOs: 25-27 and 20; or all of SEQ ID NOs: 22-27 and 19-20 encodes a murine TCR.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs (including functional portions and functional variants thereof). It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein. In this regard, the nucleic acid may consist essentially of any of the nucleotide sequences described herein.

The nucleic acids of the invention can be incorporated into a recombinant expression vector. In this regard, the invention provides a recombinant expression vector comprising any of the nucleic acids of the invention. In an embodiment of the invention, the recombinant expression vector comprises a nucleotide sequence encoding the α chain, the β chain, and linker peptide. For example, in an embodiment, the recombinant expression vector comprises the nucleotide sequence of SEQ ID NO: 21 (encoding α and β chains SEQ ID NOs: 11 and 12 with a linker positioned between them).

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotide, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector. In an especially preferred embodiment, the recombinant expression vector is an MSGV1 vector.

The recombinant expression vectors of the invention can be prepared using standard recombinant DNA techniques described in, for example, Green and Sambrook et al., supra.

Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein (including functional variants thereof), or to the nucleotide sequence which is complementary to or which hybridizes to the nucleotide sequence encoding the TCR, polypeptide, or protein (including functional variants thereof). The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD4^+$ T cells, $CD8^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods*, 128:189-201 (1990). In an embodiment, expansion of the numbers of T cells is carried out by culturing the T cells with OKT3 antibody, IL-2, and feeder PBMC (e.g., irradiated allogeneic PBMC).

The invention further provides an antibody, or antigen binding portion thereof, which specifically binds to a functional portion of any of the TCRs (or functional variant thereof) described herein. Preferably, the functional portion specifically binds to the cancer antigen, e.g., the functional portion comprising the amino acid sequence SEQ ID NO: 3 or 44 (CDR1 of α chain), 4 or 45 (CDR2 of α chain), 5 or 46 (CDR3 of α chain), 6 or 47 (CDR1 of β chain), 7 or 48 (CDR2 of β chain), 8 or 49 (CDR3 of β chain), SEQ ID NO: 9 or 50 (variable region of α chain), SEQ ID NO: 10 or 51

(variable region of β chain), or a combination thereof, e.g., 3-5; 44-46; 6-8; 47-49; 3-8; 44-49; 9; 10; 50; 51; 9-10 or 50-51. More preferably, the functional portion comprises the amino acid sequences of SEQ ID NOs: 3-8, SEQ ID NOs: 44-49, SEQ ID NOs: 9 and 10, or SEQ ID NOs: 50 and 51. In a preferred embodiment, the antibody, or antigen binding portion thereof, binds to an epitope which is formed by all 6 CDRs (CDR1-3 of the α chain and CDR1-3 of the β chain). The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive TCR (or functional variant thereof). Desirably, the antibody is specific for the functional portion of the inventive TCR (or functional variants thereof), such that there is minimal cross-reaction with other peptides or proteins.

Methods of testing antibodies for the ability to bind to any functional portion or functional variant of the inventive TCR are known in the art and include any antibody-antigen binding assay, such as, for example, radioimmunoassay (RIA), ELISA, Western blot, immunoprecipitation, and competitive inhibition assays.

Suitable methods of making antibodies are known in the art. For instance, standard hybridoma methods are described in, e.g., C. A. Janeway et al. (eds.), *Immunobiology*, 8$^{th}$ Ed., Garland Publishing, New York, NY (2011)). Alternatively, other methods, such as EBV-hybridoma methods, methods of producing antibodies in non-human animals, and bacteriophage vector expression systems are known in the art.

Phage display can also be used to generate the antibody of the invention. In this regard, phage libraries encoding antigen-binding variable (V) domains of antibodies can be generated using standard molecular biology and recombinant DNA techniques (see, e.g., Green and Sambrook et al. (eds.), *Molecular Cloning, A Laboratory Manual*, 4$^{th}$ Edition, Cold Spring Harbor Laboratory Press, New York (2012)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra).

Methods for generating humanized antibodies are well known in the art. Antibodies can also be produced by transgenic mice that are transgenic for specific heavy and light chain immunoglobulin genes. Such methods are known in the art and described in, for example, Janeway et al., supra.

The invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology. Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive TCRs, polypeptides, proteins, (including functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 80%, 90%, 95%, or can be 100%.

The inventive TCRs, polypeptides, proteins (including functional variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, functional portions, functional variants, nucleic acids, expression vectors, host cells (including populations thereof), and antibodies (including antigen binding portions thereof) described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs (including functional portions and functional variants thereof). Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for oral, parenteral, subcutaneous, intravenous, intramuscular, intraarterial, intrathecal, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell expressing the inventive TCR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A injection (Baxter, Deerfield, IL), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen (e.g., human TG), or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR (or functional variant or functional portion thereof), polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the cancer being treated. In an embodiment in which the inventive TCR material is a population of cells, the number of cells administered per infusion may vary, e.g., from about $1 \times 10^6$ to about $1 \times 10^{12}$ cells or more. In certain embodiments, fewer than $1 \times 10^6$ cells may be administered.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a targeting moiety. The practice of conjugating compounds, e.g., inventive TCR materials, to targeting moieties is known in the art. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T cell receptor (TCR), B-cell receptor (BCR), CD28, Platelet-derived Growth Factor Receptor (PDGF), nicotinic acetylcholine receptor (nAChR), etc.). The term "bridge" as used herein, refers to any agent or molecule that links the inventive TCR materials to the targeting moiety. One of ordinary skill in the art recognizes that sites on the inventive TCR materials, which are not necessary for the function of the inventive TCR materials, are ideal sites for attaching a bridge and/or a targeting moiety, provided that the bridge and/or targeting moiety, once attached to the inventive TCR materials, do(es) not interfere with the function of the inventive TCR materials, i.e., the ability to bind to TG or to detect, treat, or prevent cancer.

It is contemplated that the inventive pharmaceutical compositions, TCRs (including functional variants thereof), polypeptides, proteins, nucleic acids, recombinant expression vectors, host cells, or populations of cells can be used in methods of treating or preventing cancer. Without being bound to a particular theory, the inventive TCRs (and functional variants thereof) are believed to bind specifically to TG, such that the TCR (or related inventive polypeptide or protein and functional variants thereof), when expressed by a cell, is able to mediate an immune response against a target cell expressing TG. In this regard, the invention provides a method of treating or preventing cancer in a mammal, comprising administering to the mammal any of the pharmaceutical compositions, TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a recombinant vector which encodes any of the TCRs (and functional variants thereof), polypeptides, or proteins described herein, in an amount effective to treat or prevent cancer in the mammal.

An embodiment of the invention provides any of the pharmaceutical compositions, TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a recombinant vector which encodes any of the TCRs (and functional variants thereof), polypeptides, or proteins described herein, for use in the treatment or prevention of cancer in a mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof.

Also provided is a method of detecting the presence of cancer in a mammal. The method comprises (i) contacting a sample comprising one or more cells from the mammal with any of the inventive TCRs (and functional variants thereof), polypeptides, proteins, nucleic acids, recombinant expression vectors, host cells, populations of cells, antibodies, or antigen binding portions thereof, or pharmaceutical compositions described herein, thereby forming a complex, and detecting the complex, wherein detection of the complex is indicative of the presence of cancer in the mammal.

With respect to the inventive method of detecting cancer in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs (and functional variants thereof), polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, neuroblastoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is thyroid cancer or neuroblastoma.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

EXAMPLES

The following materials and methods were employed in Examples 1-7.

Cell Lines, Tissues, Peptides, & Antibodies

The Hurthle Carcinoma Cell line XTC (Endocrine Surgery Branch, NCI) was maintained in Dulbecco's Modified Eagle's Medium (DMEM) (Life Technologies, Carlsbad, CA) including 10% fetal bovine serum (FBS; Sigma, St. Louis, MO), 10 IU/L thyroid stimulating hormone (TSH; Sigma-Aldrich), Insulin-Transferrin-Selenium (Life Technologies). HLA-A2-expressing XTC (XTC/A2) was established by transducing XTC with retrovirus containing HLA-A*0201 (Surgery Branch, NCI). The cell lines used included: melanoma lines 624 and 938, which were generated in the Surgery Branch from resected tumors as described in Topalian et al., *J. Immunol.*, 142(10): 3714-25 (1989), Cos7, T2, and 293GP cell lines were obtained from Surgery Branch, NCI. Normal human primary cultures including fibroblasts (Surgery Branch, NCI) and small airway epithelial cells (Lonza, Walkersville, MD) were used as controls in experiments and maintained in RPMI 1640 medium (Life Technologies) with 10% FBS. Control tumor lines used included: MDA231 (breast adenocarcinoma; HLA-A2$^+$), MDA468 (breast adenocarcinoma; HLA-A2$^-$), H2087 (lung carcinoma; HLA-A2$^+$), BE-3 (Barrett's esophagus-associated adenocarcinoma of the distal esophagus; HLA-A2$^+$), SK-BR3 (breast adenocarcinoma; HLA-A2$^-$), SK-OV3 (ovarian adenocarcinoma; HLA-A2$^-$) BIC (human esophageal adenocarcinoma; HLA-A2$^+$), and four renal cell carcinoma lines (HLA-A2$^+$; Surgery Branch, NCI).

All peptides (Pi Prometrics, Huntsville, AL) were synthesized based on an HLA-A*0201 binding algorithm. The twenty best HLA-A2 binding 9-mers and ten best 10-mers were chosen for in vitro stimulation. Peptides 1-8 represent the following epitopes of TG: 1-TLLASICWV (SEQ ID NO: 29), 2-NLFGGKFLV (SEQ ID NO: 2), 3-ELPEFLLFL (SEQ ID NO: 30), 4-ALVLEIFTL (SEQ ID NO: 31), 5-ILQRRFLAV (SEQ ID NO: 32), 6-ALLRSGPYM (SEQ ID NO: 33), 7-LVEIFTLL (SEQ ID NO: 34), 8-VQQVQCWCV (SEQ ID NO: 35).

TAQMAN Real-Time Quantitative Polymerase Chain Reaction (RT-qPCR)

RNA was collected from surgically resected tissues or purchased commercially (Clonetech, Mountain View, CA). Complementary DNA (cDNA) was synthesized by the high-capacity cDNA Reverse Transcription Kit or SUPERSCRIPT III First-Strand cDNA synthesis system (Life Technologies). The following RT-PCR TAQMAN probes for comparison of antigens were used: 3' TG (00968047 ml), TPO (Hs00374163_A1), IYD (Hs00416923_A1), FOXE1 (Hs00915085_S1), and PAX8 (Hs00247586_ml), ACTB (Hs03023880_g1) (Life Technologies). For TG, a custom-designed TAQMAN primer/probe was also used to evaluate low expression of TG in a normal tissue panel. Absolute copy number was calculated based on standard curves generated by using a plasmid encoding each cDNA as a reference on the 7500 FAST Real-time PCR system (Life Technologies).

Preparation of Adenovirus

Normal thyroid total RNA was purified from a surgical specimen using RNEASY mini kit (Qiagen, Valencia, CA) and random hexamer-primed cDNA was synthesized by the SUPERSCRIPT III First-Strand cDNA synthesis system (Life Technologies). Two short cDNA fragments ($TG_{42\text{-}2186}$ and $TG_{2172\text{-}4292}$) from the 5' half of $TG_{42\text{-}8348}$ were PCR-amplified and cloned into the pShuttle2 vector by using an In-Fusion cloning kit (Clontech). After sequence confirmation, production of TG protein was examined by transfecting the pShuttle2/$TG_{42\text{-}4292}$ plasmid into HEK 293 cells and by conducting Western blotting (antibody: sc-7836, Santa Cruz Biotechnology). From the pShuttle2/$TG_{42\text{-}4292}$ plasmid, cytomegalovirus (CMV) promoter-$TG_{42\text{-}4292}$ fragment was obtained by restriction enzyme digestion and was cloned into the pAdeno-X plasmid. This plasmid was used for amplifying recombinant adenovirus according to the manufacturer's instructions (ADENO-X expression System 1, Clontech). Amplified virus was purified by ADENO-X maxi purification kit (Clontech, Mountain View, CA) and the buffer was exchanged with PBS using the PD10 gel-filtration column (GE Healthcare Life Sciences, Pittsburgh, PA). Titer of the infectious virus was measured by ADENO-X rapid titer kit (Clontech).

Immunization of Yeti/A2 Mice

Yeti mice (Stetson et al., *J. Exp. Med.,* 198(7): 1069-76 (2003)) were crossed to HLA-A*0201 transgenic mice to generate Yeti/HLA-A*0201 (Yeti/A2). The mice were also transgenic for an IFN-γ reporter gene, yellow fluorescent protein (YFP). In the Yeti system, the expression of YFP is driven by the IFN-γ promoter. When cells in these mice produce IFN-γ, they also express YFP which can be visualized with a fluorescent microscope or detected by fluorescence-activated cell scan (FACS). One hundred million colony forming units (CFU) of recombinant adenovirus/$TG_{42\text{-}4292}$ were used to immunize Yeti/A2 (half intravenously and the other half subcutaneously at the tail base) in two-week intervals. Two weeks after the second adenoviral immunization, splenocytes were harvested, plated onto 24-well plates at a cell concentration of one million cells/well maintained in RPMI (Life Technologies) including 10% fetal bovine serum (FBS; Life Technologies), 55 µM 2-mercaptoethanol (Life Technologies), 1 mM sodium pyruvate (Life Technologies), 1× MEMnon-essential amino acids (Life Technologies), 10 µg/mL gentamicin (Life Technologies), 10 U/mL penicillin, 100 µg/mL streptomycin (Life Technologies), and 250 ng/mL amphotericin B (Life Technologies) with recombinant human interleukin (IL)-2 (30 IU/ml). Individual peptides were added at a final concentration of 1 µM. Re-stimulation at one week was carried out as detailed below. HLA-A*0201 positive, Epstein-Barr Virus transformed B lymphoblastoid T2 cells were irradiated at 100 Gy and were pulsed with each peptide at a concentration of 1 µM for two hours at room temperature. After washing three times with the culture medium, T2 cells were added to Yeti splenocytes at the approximate cell number ratio of 1 to 1. Two days after the second in vitro stimulation, yellow fluorescent protein (YFP) expression was analyzed by fluorescent microscopy (AX10, Zeiss) and flow cytometry (FACS; FACSCANTO II system, BD Biosciences). Cultures with YFP expression were selected for co-culture with TG-expressing targets (XTC/A2 and CosA2 transfected to express TG) and reactivity was examined by IFN-γ secretion. RNA was purified from cultures with TG-reactivity using an RNEASY kit for the purpose of cloning T-cell receptor genes.

Generation of Retroviral Supernatant

Retroviral supernatants were generated in 293GP cells by co-transfection with the retroviral vector encoding the anti-TG-TCR and an envelope protein (RD114) using LIPOFECTAMINE 2000 reagent (Life Technologies) as described in Robbins et al., *J. Clin. Oncol.,* 29(7): 917-24 (2011). On the next day of lipofection, medium was replaced with fresh medium. The supernatant was harvested after 48 hours (h) and used to transduce anti-CD3-stimulated peripheral blood lymphocytes (PBL).

Retroviral Transduction of Anti-CD3 Stimulated PBL

All PBL were collected via leukapheresis from patients enrolled in Institutional Review Board-approved studies. Lymphocytes were cultured as described in Cohen et al., *Cancer Res.,* 66(17): 8878-86 (2006) using AIM V media (Life Technologies) containing 5% human serum (Valley Biomedical Inc., Winchester, VA) and IL-2 (Prometheus, San Diego CA) at a concentration of 300 IU/ml for PBL. PBL from allogeneic donors were stimulated with soluble anti-CD3 (OKT3, 50 ng/mL) and IL-2 (300 IU/mL) for two days before transduction was performed. After stimulation, cells were added to 24-well plates initially coated with RETRONECTIN reagent (10 µg/mL in 400 µL of PBS; Takara Shuzo, Japan) and subsequently loaded with virus by adding the virus-containing culture supernatant and centrifugating (2000×g 32° C., 2 h). After loading the virus, stimulated PBL were added at a concentration of $5 \times 10^5$ cells per well and the plates were centrifuged at 1000×g for 10 minutes (min). Plates were incubated overnight at 37° C. in 5% $CO_2$ incubator. On the following day, cells were transferred to new RETRONECTIN reagent-coated and virus-loaded 24-well plates, and the second transduction was performed. Cells were maintained at a cell density between 0.5-$1 \times 10^6$ cells/mL. Transduction efficiency was confirmed by FACS analysis of mouse TCR-β expression in transduced PBL.

Cytokine Release Assay

Interferon (IFN)-γ release by transduced PBL was determined as previously described in Wang et al., *J. Immunol. Methods,* 366(1-2): 43-51 (2011). Briefly, retrovirally-transduced cells ($1 \times 10^5$) were co-cultured with $5 \times 10^4$ target cells (XTC, XTC/A2, CosA2, or CosA2 transfected with TG) or control tumor cell lines for 18-22 hrs in RPMI with 10% FBS at 37° C., 5% $CO_2$. On the subsequent day, IFN-γ secretion was determined by enzyme-linked immunosorbent assay (ELISA).

Example 1

This example demonstrates that TG is expressed in normal tissues, primary thyroid cancer, and lymph node metastases.

Figure 1B:
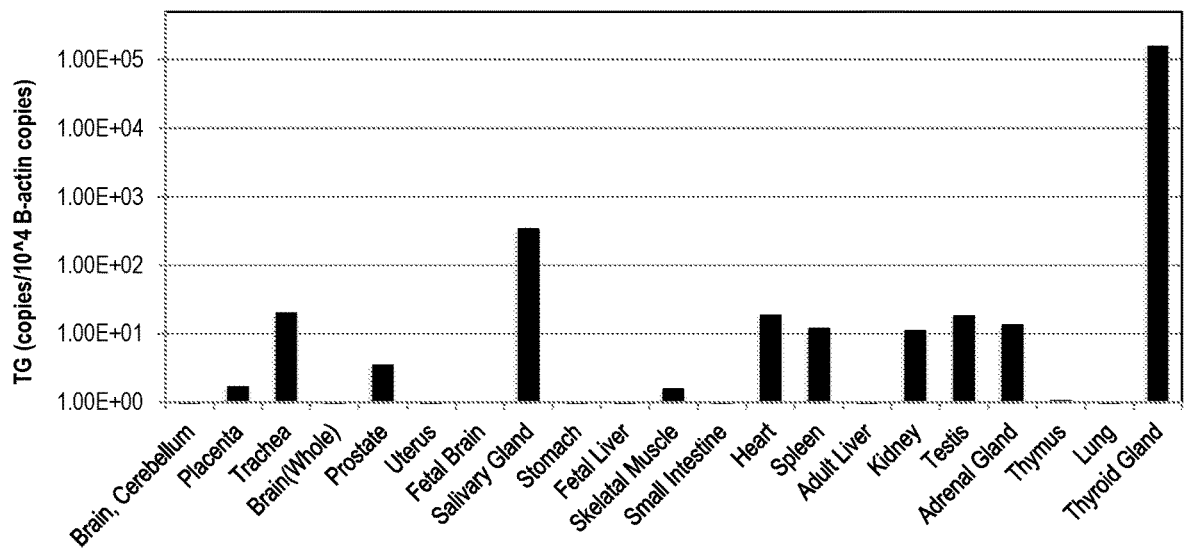
FIG. 1B is a graph showing the number of copies of TG RNA relative to $1 \times 10^4$ copies of R-actin RNA measured in various normal tissue samples.

Expression of thyroid-specific antigens, including thyroid peroxidase (TPO), paired box 8 (PAX8), forkhead box E1 (FOXE1), iodotyrosine deiodinase (IYD) and thyroglobulin (TG) (van Staveren et al., *Cancer Res.,* 67(17): 8113-20 (2007)), was investigated by TAQMAN quantitative RT-PCR. Of all of these thyroid-specific antigens, TG maintained the highest expression in normal thyroid, primary thyroid cancer, and lymph node metastases of thyroid cancer (FIG. 1A). Low expression of TG was observed in non-thyroid, normal human tissue. TG expression in thyroid tissue was higher than expression in other normal tissues (FIG. 1B). Based on these data, TG was identified as a candidate thyroid-specific target antigen for adoptive cellular therapy.

Example 2

This example demonstrates the stimulation of Yeti/A2 splenocytes with $TG_{470-478}$.

HLA-A0201-restricted murine T cells were generated by vaccinating Yeti mice that were transgenic for HLA-A0201 and an IFN-γ reporter gene (yellow fluorescent protein (YFP)) with an adenovirus encoding the 5' half of the TG gene ($TG_{42-4292}$). The mice were vaccinated with TG-containing adenovirus on day 0, followed by a second vaccination with the same adenovirus on day 14. On day 28, splenocytes were collected and stimulated in vitro with TG peptide immediately at the time of harvest, followed by a second in vitro TG peptide stimulation on day 35.

The expression of the IFN-γ reporter gene YFP by the Yeti/A2 splenocytes was measured by flow cytometry two days after the second in vitro stimulation. YFP expression in stimulated splenocytes was also evaluated by ultraviolet (UV)-microscopy after-co-culture with T2 cells pulsed with TG cognate peptide.

Figure 2:
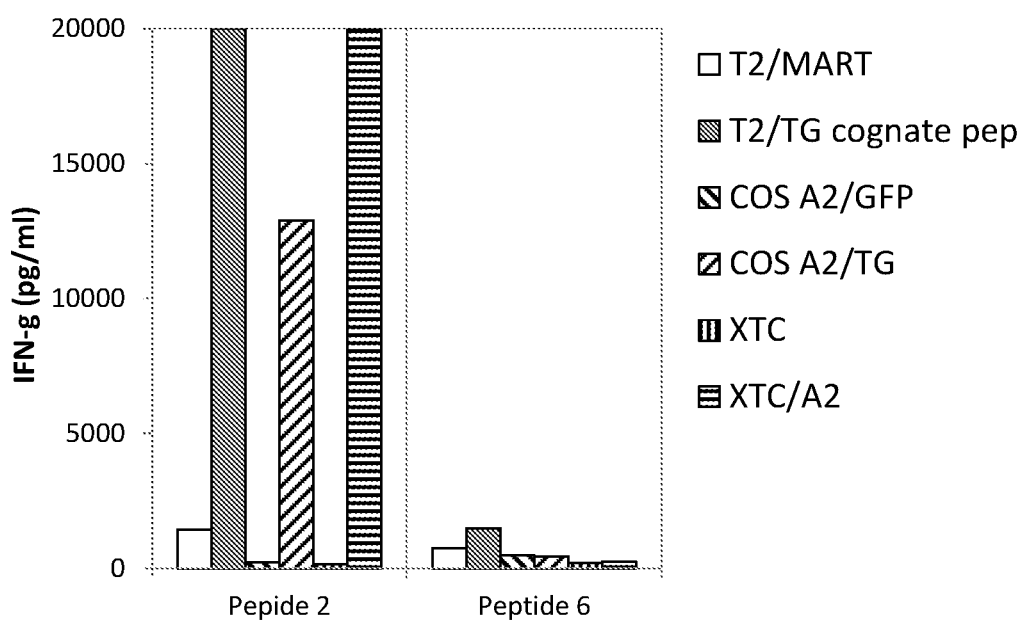
FIG. 2 is a graph showing the amount of mouse interferon (IFN)-γ (pg/ml) secreted by splenocytes from mice vaccinated with adenovirus encoding TG and stimulated twice in vitro with peptide 2 (NLFGGKFLV (SEQ ID NO: 2)) or peptide 5 (ILQRRFLAV (SEQ ID NO: 32)) when co-cultured with (identifying each bar from left to right): target T2 cells pulsed with MART-1 control peptide (T2/MART) (unshaded bars), T2 cells pulsed with TG cognate peptide (peptide 2 or 5) (grey bars), Cos7-HLA-A*0201 cells that were transfected to express control green fluorescent protein (GFP) (CosA2/GFP) (backslashed bars), Cos7-HLA-A*0201 cells that were transfected to express TG (CosA2/TG) (forward slashed bars), carcinoma cell line XTC (vertically striped bars), or XTC cells transduced to express HLA-A0201 (XTC/A2) (horizontally striped bars).

Cells that were stimulated by the peptide 2, representing the $TG_{470-478}$ epitope (NLFGGKFLV; SEQ ID NO: 2), produced a YFP signal as determined by flow cytometry and microscopy. This bulk culture was tested for reactivity against T2 cells pulsed with irrelevant (T2/MART) or the $TG_{470-478}$ peptide (T2/TG), COSA2 cells transfected with GFP or TG cDNA (CosA2/GFP and CosA2/TG) and XTC, $TG^+$ thyroid carcinoma cell line with or without transfection of HLA-A2. (FIG. 2). Peptide 2-stimulated splenocytes showed strong reactivity to XTC/A2 cells, CosA2/TG cells, and T2 cells pulsed with cognate peptide.

Example 3

This example demonstrates the isolation of the murine anti-TG TCR from the $TG_{470-478}$-stimulated splenocytes of Example 2.

Total RNA was isolated from the bulk culture by an RNEASY RNA isolation kit (Qiagen). Amplification of the 5' cDNA ends of the TCR α and β chains was done by SMARTER 5' RACE kit (Clontech) using the following primers: Universal Primer A Mix (Clonetech), α-specific primer 5'-GGCTACTTTCAGCAGGAGGA-3' (SEQ ID NO: 36), β-specific primer 5' AGGCCTCTGCACT-GATGTTC-3' (SEQ ID NO: 37). TCR α and β cDNA molecules were then inserted into a TOPO vector by TA cloning. Plasmids from 48 individual colonies for α- and β-chains were purified and sequenced. This sequence analysis revealed oligo-clonality, with 27/48 colonies of a representing TRAV3D-3*02/J22*01, 21/48 colonies of α representing TRAV15N-1*01, and 45/47 colonies of R representing TRBV26*01/D2*01/J2-5*01. Since TRAV15N-1*01 was a nonproductive recombination, it was disregarded. Based on the sequencing data, the following primers were synthesized (Life Technologies): TCR α forward (SEQ ID NO: 38) and TCR α reverse (SEQ ID NO: 39) for the α chain and TCR β forward (SEQ ID NO: 43) and TCR β reverse (SEQ ID NO: 40) for the β chain. By RT-PCR, full length cDNA of the α chain and β chain were isolated. The α chain and β chain cDNA encoded SEQ ID NOs: 11 and 12, respectively.

Example 4

This example demonstrates the generation of a retroviral recombinant expression vector encoding the murine anti-TG TCR of Example 3.

After the isolation of the full length α chain and β chain as described in Example 3, a self-cleaving 2A peptide sequence was introduced into the 5' of β chain using a 7:2:1 molar ratio mix of SEQ ID NOs: 41, 42 and 43 as the forward primer and SEQ ID NO: 40 as the reverse primer.

After the amplification, the α-chain and 2A-β-chain were cloned into the retroviral vector, MSGV1 (SEQ ID NO: 21), which is a derivative of the murine stem cell virus-based retroviral vector pMSGV (Zhao et al., *J. Immunol.*, 174(7): 4415-23 (2005)) by the IN-FUSION reaction (Clontech). The plasmid encoding the mouse anti-TG TCR was a 7394 base pair (bp) sequence encoding the α and β-chains (SEQ ID NOs: 11 and 12, respectively) separated by a self-cleaving p2A region (SEQ ID:NO 28). The sequence of the plasmid was confirmed by Sanger sequencing.

Example 5

This example demonstrates the transduction of donor PBL with a retroviral vector encoding the murine anti-TG TCR.

Anti-CD3 stimulated, human donor PBL were retrovirally transduced with the vector of Example 4. Three days after transduction, FACS analysis was performed by labeling the T-cells with antibodies against CD3, CD8, and the mouse TCR-β chain or MART-1/HLA-A2 tetramer. The efficiency of transduction of PBL from three donor patients was high (80-90%) without significant differences between CD4+ and CD8+ T-cells. The experiments were performed more than five times, each of which gave similar results.

Example 6

This example demonstrates the reactivity of the murine anti-TG TCR against HLA-A*0201$^+$/TG$^+$ targets.

Figure 3A:
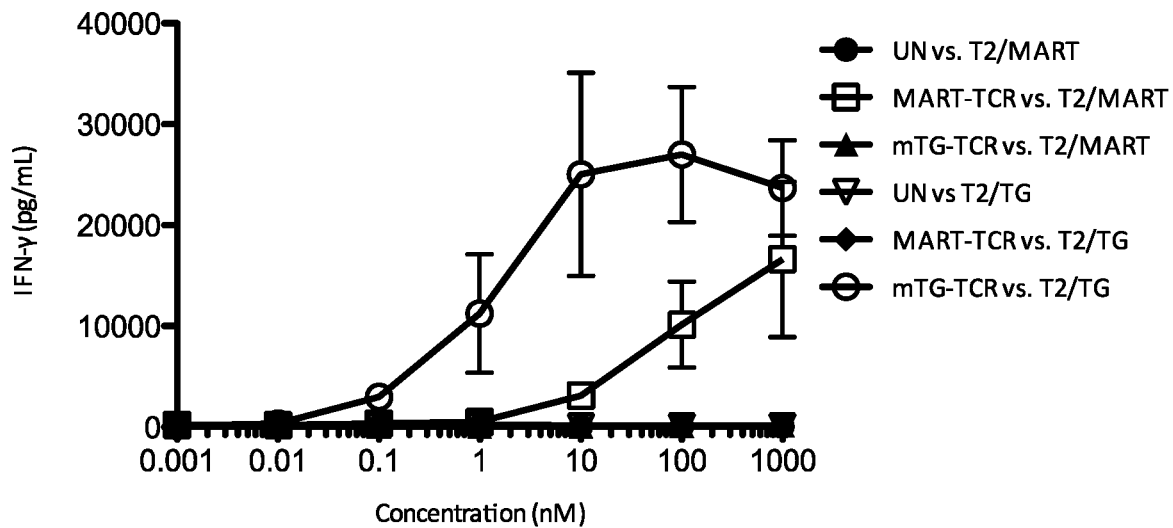
FIG. 3A is a graph showing the amount of IFN-γ (pg/ml) measured upon co-culture of effector untransduced (UN) PBL with target T2 cells pulsed with various concentrations (nM) of MART-1 peptide (closed circles) or TG peptide NLFGGKFLV (SEQ ID NO: 2) (open triangles), effector anti-MART-1 TCR-transduced PBL with target T2 cells pulsed with various concentrations of MART-1 peptide (open squares) or TG peptide NLFGGKFLV (SEQ ID NO: 2) (diamonds), or effector murine anti-TG TCR (mTG-TCR) (SEQ ID NOs: 11 and 12)-transduced PBL with target T2 cells pulsed with various concentrations of MART-1 peptide (closed triangles) or TG peptide NLFGGKFLV (SEQ ID NO: 2) (open circles).

Anti-CD3 stimulated PBL were transduced with the retroviral vector encoding the murine anti-TG TCR of Example 4 or an anti-MART-1 TCR. Untransduced cells were used as a control. Three days after transduction, $1\times10^5$ transduced cells or control cells were co-cultured with $5\times10^4$ T2 cells that had been pulsed with either TG (NLFGGKFLV (SEQ ID NO: 2)) (T2/TG) or MART-1 (T2/MART-1) peptides. PBL expressing the murine anti-TG TCR (SEQ ID NOs: 11 and 12) recognized the peptide at very low concentrations (<0.1 nM), out-performing the anti-MART-1 TCR control. (FIG. 3A).

Figure 3B:
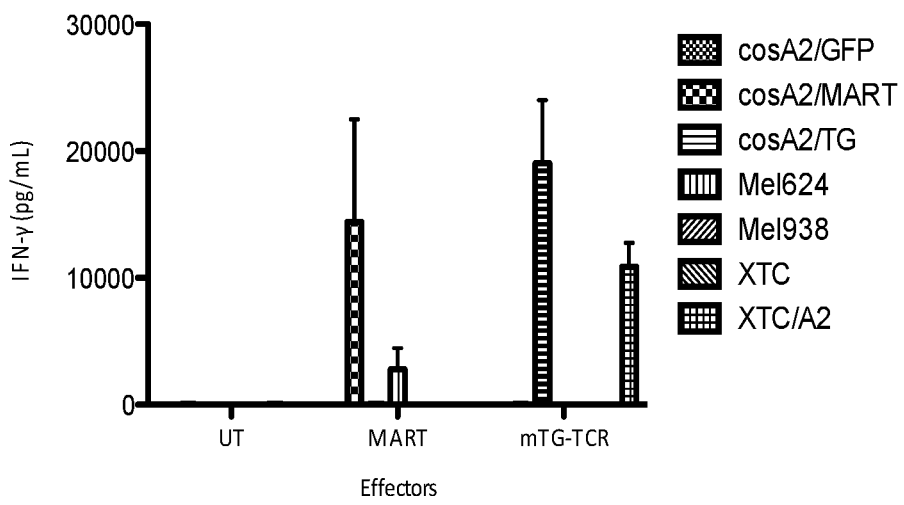
FIG. 3B is a graph showing the amount of IFN-γ (pg/ml) measured upon co-culture of effector untransduced (UT) PBL or PBL transduced with an anti-MART-1 TCR (MART) or the murine anti-TG TCR (mTG-TCR) (SEQ ID NOs: 11 and 12) with target cells CosA2/GFP cells (small checkered bars), CosA2/MART cells (large checkered bars), CosA2/TG cells (horizontally striped bars), 624Mel cells (vertically striped bars), 938Mel cells (a melanoma-derived cell line that does not express MART-1) (forward slashed bars)), XTC cells (backslashed bars), or XTC/A2 cells (boxed bars).

PBL transduced with a vector encoding the murine anti-TG TCR (SEQ ID NOs: 11 and 12) were analyzed for reactivity, as determined by human (h) IFN-γ release, after co-culture with tumor cell lines or cell lines transfected to express TG. High levels of IFN-γ were released by the PBL transduced with a vector encoding the murine anti-TG TCR (SEQ ID NOs: 11 and 12) in response to HLA-A2$^+$ TG$^+$ lines, including XTC/A2 and CosA2/TG. (FIG. 3B).

Example 7

This example demonstrates the specificity of the murine anti-TG TCR for HLA-A*0201$^+$/TG$^+$ targets.

The specificity of the murine anti-TG TCR (SEQ ID NOs: 11 and 12) was tested by analyzing its reactivity against XTC, XTC/A2, and a panel of cell lines and normal tissues not expressing one or both of TG and HLA-A*0201, including H2087, BIC, BE-3, SK-OV3, SK-BR3, MDA231, MDA468, four renal cell carcinoma lines, normal human fibroblasts, and small airway epithelial epithelium cells (Table 1). As shown in Table 1, all cell lines were one or both of HLA-A*0201$^-$ and TG$^-$, except XTC/A2. The PBL transduced with a vector encoding the murine anti-TG TCR (SEQ ID NOs: 11 and 12) showed reactivity only to the HLA-A2+/TG+ XTC/A2 cell line, and showed no reactivity to any TG-negative or HLA-A*0201-negative cell lines. Further testing of the murine anti-TG TCR against TG-expressing, freshly resected, normal, primary thyroid tissues from an HLA-A*0201⁻ patient and a HLA-A*0201⁺ patient demonstrated that the murine anti-TG TCR transduced PBL were reactive against HLA-A*0201⁺/TG⁺, but not HLA-A*0201⁻/TG⁺ tissue by IFN-γ secretion.

TABLE 1

| Cell Line | HLA-A2+ | Tg+ |
|---|---|---|
| XTC | − | + |
| XTC/A2 | + | + |
| mel624 | + | − |
| mel938 | + | − |
| Fibroblasts | + | − |
| Small Airway Epithelial Cells | − | − |
| MDA231 | + | − |
| MDA468 | − | − |
| SK-OV3 | − | − |
| SK-BR3 | − | − |
| H2087 | + | − |
| BE-3 | + | − |
| BIC | + | − |
| RCC #1 | + | − |
| RCC #2 | + | − |
| RCC #3 | + | − |
| RCC #4 | + | − |

Example 8

This example demonstrates the isolation of a human anti-TG TCR and the transduction efficiency of the human anti-TG TCR into PBL.

Human PBL were individually stimulated four times with 30 computer algorithmically-predicted HLA-A2 high binding peptides derived from $TG_{42-4292}$. After four in vitro stimulations, $TG_{3-11}$ peptide (LVLEIFTLL, SEQ ID NO: 58)-stimulated culture showed reactivity against XTC/A2. Limiting dilution cloning was carried out for this culture and one of 28 clones analyzed, clone 14, was found to have TG-specific reactivity. After the expansion of the cells, TCR α and β genes were cloned by 5'RACE followed by RT-PCR (encoding SEQ ID NOs: 54 and 55, respectively). PBL were transduced with the retroviral expression vector encoding the human anti-TG TCR.

Transduction efficiency of human anti-TG TCR expression in transduced PBL was confirmed by FACS analysis. The efficiency of transduction of PBL from two donor patients was high (75-80%) without significant differences between CD4+ and CD8+ T-cells.

Example 9

This example demonstrates the reactivity of the human anti-TG TCR of Example 8.

PBL transduced with the human anti-TG TCR of Example 8 were co-cultured with T2 cells pulsed with various concentrations of MART-1 or $TG_{3-11}$ and IFN-γ was measured (pg/ml). The results are shown in Table 2A.

TABLE 2A

| Concentration of peptide pulsed | IFN-γ (pg/ml) | |
|---|---|---|
| | T2/MART-1 | $TG_{3-11}$ |
| 1000 nM | 73.4 | 29734.3 |
| 100 nM | 73.6 | 28600.9 |
| 10 nM | 64.7 | 16848.2 |
| 1 nM | 68.2 | 2522.1 |
| 0.1 nM | 54.5 | 325.5 |
| 0.01 nM | 89.2 | 93.2 |
| 0.001 nM | 81.8 | 72.9 |
| 0 nM | 70.3 | 75.7 |

PBL transduced with the murine anti-TG TCR of Example 3 were co-cultured with T2 cells pulsed with various concentrations of MART-1 or $TG_{470-478}$. The results are shown in Table 2B.

TABLE 2B

| Concentration of peptide pulsed | IFN-γ (pg/ml) | |
|---|---|---|
| | T2/MART-1 | $T2/TG_{470-478}$ |
| 1000 nM | 373.7 | 47261.6 |
| 100 nM | 125.8 | 33459.2 |
| 10 nM | 50.2 | 27326.8 |
| 1 nM | 41.5 | 13124.8 |
| 0.1 nM | 36.5 | 8680 |
| 0.01 nM | 41 | 1236.8 |
| 0.001 nM | 38.2 | 136.1 |
| 0 nM | 37.7 | 55.8 |

As shown in Tables 2A and 2B, although the reactivity of the murine anti-TG TCR was superior to that of the human anti-TG TCR, PBL transduced with the human anti-TG TCR were reactive against cells pulsed with $TG_{3-11}$.

PBL transduced with the human anti-TG TCR of Example 8 or the murine anti-TG TCR of Example 3 were co-cultured with COSA2/GFP cells, COSA2/TG cells, 624Mel cells, XTC cells, or XTC/A2 cells, and IFN-γ was measured (pg/ml). The results are shown in Table 3.

TABLE 3

| | IFN-γ (pg/ml) | | | | |
|---|---|---|---|---|---|
| | COSA2/GFP | COSA2/TG | 624Mel | XTC | XTC/A2 |
| human anti-TG TCR | 15.5 | 8794.7 | 1.8 | 5.7 | 735.3 |
| murine anti-TG TCR | 19.2 | 25298.4 | 7.2 | 2.3 | 21371.9 |

As shown in Table 3, although the reactivity of the murine anti-TG TCR was superior to that of the human anti-TG TCR, PBL transduced with the human anti-TG TCR were reactive against HLA-A2+/TG+ cell lines.

In a separate experiment, PBL from two patients that were untransduced (UT) or transduced with the human anti-TG TCR of Example 8, the murine anti-TG TCR of Example 3, or an anti-MART-1 TCR were co-cultured with COSA2/GFP cells, COSA2/MART-1 cells, Cos7-HLA-A*01 cells that were transfected to express TG (COSA1/TG cells), COSA2/TG cells, 624Mel cells (MART-1+), 938Mel cells, XTC cells, or XTC/A2 cells, and IFN-γ was measured (pg/ml). The results are shown in Table 4A (Patient 1) and Table 4B (Patient 2).

TABLE 4A

| | IFN-γ (pg/ml) | | | |
|---|---|---|---|---|
| | UT | Anti-MART-1 TCR | human anti-TG TCR | murine anti-TG TCR |
| COSA2/GFP | 0 | 0 | 0 | 0 |
| COSA2/MART-1 | 0 | 20000 | 0 | 0 |
| COSA1/TG | 0 | 0 | 0 | 0 |
| COSA2/TG | 0 | 0 | 15500 | 20000 |
| 624Mel | 0 | 7000 | 0 | 0 |
| 938Mel | 0 | 0 | 0 | 0 |
| XTC | 0 | 0 | 0 | 0 |
| XTC/A2 | 0 | 0 | 500 | 20000 |

TABLE 4B

| | IFN-γ (pg/ml) | | | |
|---|---|---|---|---|
| | UT | Anti-MART-1 TCR | human anti-TG TCR | murine anti-TG TCR |
| COSA2/GFP | 0 | 0 | 0 | 0 |
| COSA2/MART-1 | 0 | 20000 | 0 | 0 |
| COSA1/TG | 0 | 0 | 0 | 0 |
| COSA2/TG | 0 | 0 | 14800 | 20000 |
| 624Mel | 0 | 3800 | 0 | 0 |
| 938Mel | 0 | 0 | 0 | 0 |
| XTC | 0 | 0 | 0 | 0 |
| XTC/A2 | 0 | 0 | 300 | 17900 |

Further testing of the human anti-TG-TCR against TG-expressing, freshly resected, normal, primary thyroid tissues from an HLA-A*0201⁻ patient and a HLA-A*0201⁺ patient demonstrated that the human anti-TG-TCR transduced PBL were reactive against HLA-A*0201⁺/TG⁺, but not HLA-A*0201⁻/TG⁺ tissue, as measured by IFN-γ secretion.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

SEQUENCE LISTING

```
Sequence total quantity: 58
SEQ ID NO: 1              moltype = AA   length = 2768
FEATURE                   Location/Qualifiers
source                    1..2768
                          mol_type = protein
                          organism = Homo sapiens
SEQUENCE: 1
MALVLEIFTL LASICWVSAN IFEYQVDAQP LRPCELQRET AFLKQADYVP QCAEDGSFQT   60
VQCQNDGRSC WCVGANGSEV LGSRQPGRPV ACLSFCQLQK QQILLSGYIN STDTSYLPQC  120
QDSGDYAPVQ CDVQQVQCWC VDAEGMEVYG TRQLGRPKRC PRSCEIRNRR LLHGVGDKSP  180
PQCSAEGEFM PVQCKFVNTT DMMIFDLVHS YNRFPDAFVT FSSFQRRFPE VSGYCHCADS  240
QGRELAETGL ELLLDEIYDT IFAGLDLPST FTETTLYRIL QRRFLAVQSV ISGRFRCPTK  300
CEVERFTATS FGHPYVPSCR RNGDYQAVQC QTEGPCWCVD AQGKEMHGTR QGEPPSCAE  360
GQSCASERQQ ALSRLYFGTS GYFSQHDLFS SPEKRWASPR VARFATSCPP TIKELFVDSG  420
LLRPMVEGQS QQFSVSENLL KEAIRAIFPS RGLARLALQF TTNPKRLQQN LFGGKFLVNV  480
GQFNLSGALG TRGTFNFSQF FQQLGLASFL NGGRQEDLAK PLSVGLDSNS STGTPEAAKK  540
DGTMNKPTVG SFGFEINLQE NQNALKFLAS LLELPEFLLF LQHAISVPED VARDLGDVME  600
TVLSSQTCEQ TPERLFVPSC TTEGSYEDVQ CFSGECWCVN SWGKELPGSR VRGGQPRCPT  660
DCEKQRARMQ SLMGSQPAGS TLFVPACTSE GHFLPVQCFN SECYCVDAEG QAIPGTRSAI  720
GKPKKCPTPC QLQSEQAFLR TVQALLSNSS MLPTLSDTYI PQCSTDGQWR QVQCNGPPEQ  780
VFELYQRWEA QNKGQDLTPA KLLVKIMSYR EAASGNFSLF IQSLYEAGQQ DVFPVLSQYP  840
SLQDVPLAAL EGKRPQPREN ILLEPYLFWQ ILNGQLSQYP GSYSDFSTPL AHFDLRNCWC  900
VDEAGQELEG MRSEPSKLPT CPGSCEEAKL RVLQFIRETE EIVSASNSSR FPLGESFLVA  960
KGIRLRNEDL GLPPLFPPRE AFAEQFLRGS DYAIRLAAQS TLSFYQRRRF SPDDSAGASA 1020
LLRSGPYMPQ CDAFGSWEPV QCHAGTGHCW CVDEKGGFIP GSLTARSLQI PQCPTTCEKS 1080
RTSGLLSSWK QARSQENPSP KDLFVPACLE TGEYARLQAS GAGTWCVDPA SGEELRPGSS 1140
```

```
SSAQCPSLCN VLKSGVLSRR VSPGYVPACR AEDGGFSPVQ CDQAQGSCWC VMDSGEEVPG 1200
TRVTGGQPAC ESPRCPLPFN ASEVVGGTIL CETISGPTGS AMQQCQLLCR QGSWSVFPPG 1260
PLICSLESGR WESQLPQPRA CQRPQLWQTI QTQGHFQLQL PPGKMCSADY ADLLQTFQVF 1320
ILDELTARGF CQIQVKTFGT LVSIPVCNNS SVQVGCLTRE RLGVNVTWKS RLEDIPVASL 1380
PDLHDIERAL VGKDLLGRFT DLIQGSFQL HLDSKTFPAE TIRFLQGDHF GTSPRTWFGC 1440
SEGFYQVLTS EASQDGLGCV KCPEGSYSQD EECIPCPVGF YQEQAGSLAC VPCPVGRTTI 1500
SAGAFSQTHC VTDCQRNEAG LQCDQNGQYR ASQKDRGSGK AFCVDGEGRR LPWWETEAPL 1560
EDSQCLMMQK FEKVPESKVI FDANAPVAVR SKVPDSEFPV MQCLTDCTED EACSFFTVST 1620
TEPEISCDFY AWTSDNVACM TSDQKRDALG NSKATSFGSL RCQVKVRSHG QDSPAVYLKK 1680
GQGSTTTLQK RFEPTGFQNM LSGLYNPIVF SASGANLTDA HLFCLLACDR DLCCDGFVLT 1740
QVQGGAIICG LLSSPSVLLC NVKDWMDPSE AWANATCPGV TYDQESHQVI LRLGDQEFIK 1800
SLTPLEGTQD TFTNFQQVYL WKDSDMGSRP ESMGCRKDTV PRPASPTEAG LTTELFSPVD 1860
LNQVIVNGNQ SLSSQKHWLF KHLFSAQQAN LWCLSRCVQE HSFCQLAEIT ESASLYFTCT 1920
LYPEAQVCDD IMESNAQGCR LILPQMPKAL FRKKVILEDK VKNFYTRLPF QKLMGISIRN 1980
KVPMSEKSIS NGFFECERRC DADPCCTGFG FLNVSQLKGG EVTCLTLNSL GIQMCSEENG 2040
GAWRILDCGS PDIEVHTYPF GWYQKPIAQN NAPSFCPLVV LPSLTEKVSL DSWQSLALSS 2100
VVVDPSIRHF DVAHVSTAAT SNFSAVRDLC LSECSQHEAC LITTLQTQPG AVRCMFYADT 2160
QSCTHSLQGQ NCRLLLREEA THIYRKPGIS LLSYEASVPS VPISTHGRLL GRSQAIQVGT 2220
SWKQVDQFLG VPYAAPPLAE RRFQAPEPLN WTGSWDASKP RASCWQPGTR TSTSPGVSED 2280
CLYLNVFIPQ NVAPNASVLV FFHNTMDREE SEGWPAIDGS FLAAVGNLIV VTASYRVGVF 2340
GFLSSGSGEV SGNWGLLDQV AALTWVQTHI RGFGGDPRRV SLAADRGGAD VASIHLLTAR 2400
ATNSQLFRRA VLMGGSALSP AAVISHERAQ QQAIALAKEV SCPMSSSQEV VSCLRQKPAN 2460
VLNDAQTKLL AVSGPHYWG PVIDGHFLRE PPARALKRSL WVEVDLLIGS SQDDGLINRA 2520
KAVKQFEESR GRTSSKTAFY QALQNSLGGE DSDARVEAAA TWYYSLEHST DDYASFSRAL 2580
ENATRDYFII CPIIDMASAW AKRARGNVFM YHAPENYGHG SLELLADVQF ALGLPFYPAY 2640
EGQFSLEEKS LSLKIMQYFS HFIRSGNPNY PYEFSRKVPT FATPWPDFVP RAGGENYKEF 2700
SELLPNRQGL KKADCSFWSK YISSLKTSAD GAKGGQSAES EEEELTAGSG LREDLLSLQE 2760
PGSKTYSK                                                        2768

SEQ ID NO: 2            moltype = AA   length = 9
FEATURE                 Location/Qualifiers
source                  1..9
                        mol_type = protein
                        organism = Homo sapiens
SEQUENCE: 2
NLFGGKFLV                                                          9

SEQ ID NO: 3            moltype = AA   length = 6
FEATURE                 Location/Qualifiers
source                  1..6
                        mol_type = protein
                        organism = Mus musculus
SEQUENCE: 3
DPNSYY                                                             6

SEQ ID NO: 4            moltype = AA   length = 7
FEATURE                 Location/Qualifiers
source                  1..7
                        mol_type = protein
                        organism = Mus musculus
SEQUENCE: 4
VFSSTEI                                                            7

SEQ ID NO: 5            moltype = AA   length = 11
FEATURE                 Location/Qualifiers
source                  1..11
                        mol_type = protein
                        organism = Mus musculus
SEQUENCE: 5
AVSSSGSWQL I                                                      11

SEQ ID NO: 6            moltype = AA   length = 5
FEATURE                 Location/Qualifiers
source                  1..5
                        mol_type = protein
                        organism = Mus musculus
SEQUENCE: 6
KGHPV                                                              5

SEQ ID NO: 7            moltype = AA   length = 6
FEATURE                 Location/Qualifiers
source                  1..6
                        mol_type = protein
                        organism = Mus musculus
SEQUENCE: 7
FQNQEV                                                             6

SEQ ID NO: 8            moltype = AA   length = 11
FEATURE                 Location/Qualifiers
```

```
source                     1..11
                           mol_type = protein
                           organism = Mus musculus
SEQUENCE: 8
ASLGGSQDTQ Y                                                              11

SEQ ID NO: 9               moltype = AA   length = 123
FEATURE                    Location/Qualifiers
source                     1..123
                           mol_type = protein
                           organism = Mus musculus
SEQUENCE: 9
MKTVTGPLFL CFWLQLNCVS RGEQVEQRPP HLSVREGDSA VIICTYTDPN SYYFFWYKQE         60
PGAGLQLLMK VFSSTEINEG QGFTVLLNKK DKQLSLNLTA AHPGDSAVYF CAVSSSGSWQ        120
LIF                                                                      123

SEQ ID NO: 10              moltype = AA   length = 123
FEATURE                    Location/Qualifiers
source                     1..123
                           mol_type = protein
                           organism = Mus musculus
SEQUENCE: 10
MATRLLCYTV LCLLGARILN SKVIQTPRYL VKGQGQKAKM RCIPEKGHPV VFWYQQNKNN         60
EFKFLINFQN QEVLQQIDMT EKRFSAECPS NSPCSLEIQS SEAGDSALYL CASLGGSQDT        120
QYF                                                                      123

SEQ ID NO: 11              moltype = AA   length = 270
FEATURE                    Location/Qualifiers
source                     1..270
                           mol_type = protein
                           organism = Mus musculus
SEQUENCE: 11
MKTVTGPLFL CFWLQLNCVS RGEQVEQRPP HLSVREGDSA VIICTYTDPN SYYFFWYKQE         60
PGAGLQLLMK VFSSTEINEG QGFTVLLNKK DKQLSLNLTA AHPGDSAVYF CAVSSSGSWQ        120
LIFGSGTQLT VMPDIQNPEP AVYQLKDPRS QDSTLCLFTD FDSQINVPKT MESGTFITDK        180
TVLDMKAMDS KSNGAIAWSN QTSFTCQDIF KETNATYPSS DVPCDATLTE KSFETDMNLN        240
FQNLSVMGLR ILLLKVAGFN LLMTLRLWSS                                         270

SEQ ID NO: 12              moltype = AA   length = 305
FEATURE                    Location/Qualifiers
source                     1..305
                           mol_type = protein
                           organism = Mus musculus
SEQUENCE: 12
MATRLLCYTV LCLLGARILN SKVIQTPRYL VKGQGQKAKM RCIPEKGHPV VFWYQQNKNN         60
EFKFLINFQN QEVLQQIDMT EKRFSAECPS NSPCSLEIQS SEAGDSALYL CASLGGSQDT        120
QYFGPGTRLL VLEDLRNVTP PKVSLFEPSK AEIANKQKAT LVCLARGFFP DHVELSWWVN        180
GKEVHSGVST DPQAYKESNY SYCLSSRLRV SATFWHNPRN HFRCQVQPHG LSEEDKWPEG        240
SPKPVTQNIS AEAWGRADCG ITSASYHQGV LSATILYEIL LGKATLYAVL VSGLVLMAMV        300
KKKNS                                                                    305

SEQ ID NO: 13              moltype = AA   length = 147
FEATURE                    Location/Qualifiers
source                     1..147
                           mol_type = protein
                           organism = Mus musculus
SEQUENCE: 13
GSGTQLTVMP DIQNPEPAVY QLKDPRSQDS TLCLFTDFDS QINVPKTMES GTFITDKTVL         60
DMKAMDSKSN GAIAWSNQTS FTCQDIFKET NATYPSSDVP CDATLTEKSF ETDMNLNFQN        120
LSVMGLRILL LKVAGFNLLM TLRLWSS                                            147

SEQ ID NO: 14              moltype = AA   length = 182
FEATURE                    Location/Qualifiers
source                     1..182
                           mol_type = protein
                           organism = Mus musculus
SEQUENCE: 14
GPGTRLLVLE DLRNVTPPKV SLFEPSKAEI ANKQKATLVC LARGFFPDHV ELSWWVNGKE         60
VHSGVSTDPQ AYKESNYSYC LSSRLRVSAT FWHNPRNHFR CQVQFHGLSE EDKWPEGSPK        120
PVTQNISAEA WGRADCGITS ASYHQGVLSA TILYEILLGK ATLYAVLVSG LVLMAMVKKK        180
NS                                                                       182

SEQ ID NO: 15              moltype = DNA   length = 369
FEATURE                    Location/Qualifiers
source                     1..369
                           mol_type = genomic DNA
                           organism = Mus musculus
SEQUENCE: 15
atgaagacag tgactggacc tttgttcctg tgcttctggc tgcagctgaa ctgtgtgagc         60
```

```
agaggcgagc aggtggagca gcgccctcct cacctgagtg tccgggaggg agacagtgcc   120
gttatcatct gcacctacac agaccctaac agttattact tcttctggta caagcaagag   180
ccggggggcag gtcttcagtt gcttatgaag gttttctcaa gtacggaaat aaacgaagga   240
caaggattca ctgtcctact gaacaagaaa gacaaacaac tctctctgaa cctcacagct   300
gcccatcctg gggactcagc cgtgtacttc tgcgcagtca gttcttctgg cagctggcaa   360
ctcatcttt                                                            369

SEQ ID NO: 16          moltype = DNA   length = 369
FEATURE                Location/Qualifiers
source                 1..369
                       mol_type = genomic DNA
                       organism = Mus musculus
SEQUENCE: 16
atggctacaa ggctcctctg ttacacagta ctttgtctcc tgggtgcaag aattttgaat   60
tcaaaagtca ttcagactcc aagatatctg gtgaaagggc aaggacaaaa agcaaagatg   120
aggtgtatcc ctgaaaaggg acatccagtt gtattctggt atcaacaaaa taagaacaat   180
gagtttaaat ttttgattaa ctttcagaat caagaagttc ttcagcaaat agacatgact   240
gaaaaacgat tctctgctga gtgtccttca aactcacctt gcagcctaga aattcagtcc   300
tctgaggcag gagactcagc actgtacctc tgtgccagcc tgggggaag ccaagacacc   360
cagtacttt                                                            369

SEQ ID NO: 17          moltype = DNA   length = 813
FEATURE                Location/Qualifiers
source                 1..813
                       mol_type = genomic DNA
                       organism = Mus musculus
SEQUENCE: 17
atgaagacag tgactggacc tttgttcctg tgcttctggc tgcagctgaa ctgtgtgagc   60
agaggcgagc aggtggagca gcgccctcct cacctgagtg tccgggaggg agacagtgcc   120
gttatcatct gcacctacac agaccctaac agttattact tcttctggta caagcaagag   180
ccggggggcag gtcttcagtt gcttatgaag gttttctcaa gtacggaaat aaacgaagga   240
caaggattca ctgtcctact gaacaagaaa gacaaacaac tctctctgaa cctcacagct   300
gcccatcctg gggactcagc cgtgtacttc tgcgcagtca gttcttctgg cagctggcaa   360
ctcatctttg gatctggaac ccaactgaca gttatgcctg acatccagaa cccagaacct   420
gctgtgtacc agttaaaaga tcctcggtc caggacagca ccctctgcct gttcaccgac   480
tttgactccc aaatcaatgt gccgaaaaac atgaatctg aacgttcat cactgacaaa   540
actgtgctgg acatgaaagc tatggattcc aagagcaatg ggccattgc ctggagcaac   600
cagacaagct tcacctgcca agatatcttc aaagagacca acgccaccta ccccagttca   660
gacgttccct gtgatgccac gttgactgag aaaagctttg aaacagatat gaacctaaac   720
tttcaaaacc tgtcagttat gggactccga atcctcctg tgaaagtagc cggatttaac   780
ctgctcatga cgctgaggct gtggtccagt tag                                 813

SEQ ID NO: 18          moltype = DNA   length = 918
FEATURE                Location/Qualifiers
source                 1..918
                       mol_type = genomic DNA
                       organism = Mus musculus
SEQUENCE: 18
atggctacaa ggctcctctg ttacacagta ctttgtctcc tgggtgcaag aattttgaat   60
tcaaaagtca ttcagactcc aagatatctg gtgaaagggc aaggacaaaa agcaaagatg   120
aggtgtatcc ctgaaaaggg acatccagtt gtattctggt atcaacaaaa taagaacaat   180
gagtttaaat ttttgattaa ctttcagaat caagaagttc ttcagcaaat agacatgact   240
gaaaaacgat tctctgctga gtgtccttca aactcacctt gcagcctaga aattcagtcc   300
tctgaggcag gagactcagc actgtacctc tgtgccagcc tgggggaag ccaagacacc   360
cagtactttg ggcaggcac tcggctcctc gtgttagagg atctgagaaa tgtgactcca   420
cccaaggtct ccttgtttga gccatcaaaa gcagagattg caaacaaaca aaaggctacc   480
ctcgtgtgct tggccagggg cttcttccct gaccacgtgg agctgagctg gtgggtgaat   540
ggcaaggagg tccacagtgg ggtcagcacg gaccctcagg cctacaagga gagcaattat   600
agctactgcc tgagcagccg cctgagggtc tctgctacct cctggcacaa tcctcgaaac   660
cacttccgct gccaagtgca gttccatggg cttcagagg aggacaagtg gccagagggc   720
tcacccaaac ctgtcacaca gaacatcagt gcagaggcct ggggccgagc agactgtgga   780
atcacttcag catcctatca tcaggggtt ctgtctgcaa ccatcctcta tgagatccta   840
ctggggaagg ccaccctata tgctgtgctg gtcagtggcc tggtgctgat ggccatggtc   900
aagaaaaaaa attcctga                                                  918

SEQ ID NO: 19          moltype = DNA   length = 441
FEATURE                Location/Qualifiers
source                 1..441
                       mol_type = genomic DNA
                       organism = Mus musculus
SEQUENCE: 19
ggatctggaa cccaactgac agttatgcct gacatccaga acccagaacc tgctgtgtac   60
cagttaaaag atcctcggtc tcaggacagc accctctgcc tgttcaccga ctttgactcc   120
caaatcaatg tgccgaaaac catgaatct ggaacgttca tcactgacaa aactgtgctg   180
gacatgaaag ctatggattc caagagcaat gggccattgc ctggagcaa ccagacaagc   240
ttcacctgcc aagatatctt caagagacc aacgccacct ccccagttc agacgttccc   300
tgtgatgcca cgttgactga gaaaagcttt gaaacagata tgaacctaaa cttctcaaaac   360
ctgtcagtta tgggactccg aatcctcctg ctgaaagtag ccggatttaa cctgctcatg   420
acgctgaggc tgtggtccag t                                              441
```

```
SEQ ID NO: 20            moltype = DNA  length = 549
FEATURE                  Location/Qualifiers
source                   1..549
                         mol_type = genomic DNA
                         organism = Mus musculus
SEQUENCE: 20
gggccaggca ctcggctcct cgtgttagag gatctgagaa atgtgactcc acccaaggtc    60
tccttgtttg agccatcaaa agcagagatt gcaaacaaac aaaaggctac cctcgtgtgc   120
ttggccaggg gcttcttccc tgaccacgtg gagctgagct ggtgggtgaa tggcaaggag   180
gtccacagtg gggtcagcac ggaccctcag gcctacaagg agagcaatta tagctactgc   240
ctgagcagcc gcctgagggt ctctgctacc ttctggcaca atcctcgaaa ccacttccgc   300
tgccaagtgc agttccatgg gctttcgag gaggacaagt ggccagaggg ctcacccaaa    360
cctgtcacac agaacatcag tgcagaggcc tggggccgag cagactgtgg aatcacttca   420
gcatcctatc atcaggggt tctgtctgca accatcctct atgagatcct actggggaag   480
gccaccctat atgctgtgct ggtcagtggc ctggtgctga tggccatggt caagaaaaaa   540
aattcctga                                                           549

SEQ ID NO: 21            moltype = DNA  length = 7394
FEATURE                  Location/Qualifiers
misc_feature             1..7394
                         note = Synthetic
source                   1..7394
                         mol_type = other DNA
                         organism = synthetic construct
SEQUENCE: 21
ccatgaagac agtgactgga cctttgttcc tgtgcttctg gctgcagctg aactgtgtga    60
gcagaggcga gcaggtggag cagcgccctc ctcacctgag tgtccgggag ggagacagtg   120
ccgttatcat ctgcacctac acagacccta acagttatta cttcttctgg tacaagcaag   180
agccgggggc aggtcttcag ttgcttatga aggttttctc aagtacggaa ataaacgaag   240
gacaaggatt cactgtccta ctgaacaaga agacaaaaca actctctctg aacctcacag   300
ctgcccatcc tggggactca gccgtgtact ctgcgcagt cagttcttct ggcagctggc   360
aactcatctt tggatctgga acccaactga cagttatgcc tgacatccag aacccagaac   420
ctgctgtgta ccagttaaaa gatcctcggt ctcaggacag caccctcctg ctgttcaccg   480
actttgactc ccaaatcaat gtgccgaaaa ccatggaatc tggaacgttc atcactgcca   540
aaactgtgct ggacatgaaa gctatggatt ccaagagcaa tggggccatt gcctggcagca   600
accagacaag cttcacctgc caagatatct tcaaagagac caacgccacc taccccagtt   660
cagacgttcc ctgtgatgcc acgttgactg agaaaagctt tgaaacagat atgaacctaa   720
actttcaaaa cctgtcagtt atgggactcc gaatcctcct gctgaaagta gccggattta   780
acctgctcat gacgctgagg ctgtggtcca gtcgggccaa gcggtccgga tccgagcca   840
ccaacttcag cctgctgaag caggccgcg acgtggagga gaaccccggc cccatgcta    900
caaggctcct ctgttacaca gtactttgtc tcctgggtgc aagaattttg aattcaaaag   960
tcattcagac tccaagatat ctggtgaaag ggcaaggaca aaagcaaag gtgaggtgta  1020
tccctgaaaa gggacatcca gttgtattct ggtatcaaca aaataagaac aatgagttta  1080
aattttgat taactttcag aatcaagaag ttcttcagca aatagacatg actgaaaaac  1140
gattctctgc tgagtgtcct tcaaactcac cttgcagcct agaaattcag tcctctgagg  1200
caggagactc agcactgtac ctctgtgcca gcctggaagc caagacc ccccagtact   1260
ttgggccagg cactcggctc ctcgtgttag aggatctgag aaatgtgact ccacccaagg  1320
tctccttgtt tgagccatca aaagcagaga ttgcaaacaa acaaaaggct ccctcgtgt  1380
gcttggccag gggcttcttc cctgaccacg tggagctgag ctggtgggtg aatggcaagg  1440
aggtccacag tgggtcagc acggaccctc aggcctacaa ggagagcaat tatagctact  1500
gcctgagcag ccgcctgagg gtctctgcta ccttctggca caatcctcga accacttcc  1560
gctgccaagt gcagttccat gggctttcag aggaggacaa gtggccagag ggctcaccca  1620
aacctgtcac acagaacatc agtgcagagg cctggggccg agcagactgt ggaatcactt  1680
cagcatccta tcatcagggg gttctgtctg caaccatcct ctatgagatc ctactgggga  1740
aggccaccct atatgctgtg ctggtcagtg gcctggtgct gatggccatg gtcaagaaaa  1800
aaaaattcctg accgaattct gcagtcgacg gtaccgcggg cccgggatcg atccgataaa  1860
ataaaagatt tatttagtc tccagaaaaa ggggggaatg aaagacccca cctgtaggtt  1920
tggcaagcta gcttaagtaa cgccattttg caaggcatgg aaaatacata actgagaata  1980
gagaagttca gatcaaggtt aggaacagag agacagcaga atatgggcca aacaggatat  2040
ctgtggtaag cagttcctgc cccggctcag ggccaagaac agatggtccc cagatgcggt  2100
cccgccctca gcagtttcta gagaaccatc agatgtttcc agggtgcccc aaggacctga  2160
aaatgaccct gtgccttatt tgaactaacc aatcagttcg cttctcgctt ctgttcgcgc  2220
gcttctgctc cccgagctca ataaaagagc ccacaacccc tcactcggcg cgccagtcct  2280
ccgatagact cgtcgcccg gtacccgtgt atccaataaa ccctcttgc agttgcatcc  2340
gacttgtggt ctcgctgttc cttgggaggg tctcctctga gtgattgact accgtcagc  2400
gggggtcttt catgggtaac agtttcttga agttggagaa caacattctg agggtaggag  2460
tcgaatatta agtaatcctg actcaattag ccactgtttt gaatccacat actccaatac  2520
tcctgaaatc catcgatgga gttcattatg gacagcgcag aaagagctgg ggagaattgt  2580
gaaattgtta tccgctcaca attccacaca acatacgagc cggaagcata agtgtaaag  2640
cctgggtgc ctaatgagtg agctaactca cattaattgc gttgcgctca ctgcccgctt  2700
tccagtcggg aaacctgtcg tgccagctgc attaatgaat cggccaacgc gcggggagag  2760
gcggtttgcg tattgggcgc tcttccgctt cctcgctcac tgactcgctg cgctcggtcg  2820
ttcggctgcg gcgagcggta tcagctcact caaaggcggt aatacggtta tccacagaat  2880
caggggataa cgcaggaaag aacatgtgag caaaaggcca gcaaaaggcc aggaaccgta  2940
aaaaggccgc gttgctggcg tttttccata ggctccgccc ccctgacgag catcacaaaa  3000
atcgacgctc aagtcagagg tggcgaaacc cgacaggact ataaagatac caggcgtttc  3060
cccctggaag ctccctcgtg cgctctcctg ttccgaccct gccgcttacc ggatacctgt  3120
ccgcctttct cccttcggga agcgtggcgc tttctcatag ctcacgctgt aggtatctca  3180
```

```
gttcggtgta ggtcgttcgc tccaagctgg gctgtgtgca cgaaccccc gttcagcccg  3240
accgctgcgc cttatccggt aactatcgtc ttgagtccaa cccggtaaga cacgacttat  3300
cgccactggc agcagccact ggtaacagga ttagcagagc gaggtatgta ggcggtgcta  3360
cagagttctt gaagtggtgg cctaactacg gctacactag aaggacagta tttggtatct  3420
gcgctctgct gaagccagtt accttcggaa aaagagttgg tagctcttga tccggcaaac  3480
aaaccaccgc tggtagcggt ggttttttg tttgcaagca gcagattacg cgcagaaaaa  3540
aaggatctca agaagatcct ttgatctttt ctacggggtc tgacgctcag tggaacgaaa  3600
actcacgtta agggattttg gtcatgagat tatcaaaaag gatcttcacc tagatccttt  3660
taaattaaaa atgaagtttt aaatcaatct aaagtatata tgagtaaact tggtctgaca  3720
gttaccaatg cttaatcagt gaggcaccta tctcagcgat ctgtctattt cgttcatcca  3780
tagttgcctg actcccgtc gtgtagataa ctacgatacg ggagggctta ccatctggcc  3840
ccagtgctgc aatgataccg cgagaccac gctcaccggc tccagattta tcagcaataa  3900
accagccagc cggaagggcc gagcgcagaa gtggtcctgc aactttatcc gcctccatcc  3960
agtctattaa ttgttgccgg gaagctagag taagtagttc gccagttaat agtttgcgca  4020
acgttgttgc cattgctaca ggcatcgtgg tgtcacgctc gtcgtttggt atggcttcat  4080
tcagctccgg ttcccaacga tcaaggcgag ttacatgatc ccccatgttg tgcaaaaaag  4140
cggttagctc cttcggtcct ccgatcgttg tcagaagtaa gttggccgca gtgttatcac  4200
tcatggttat ggcagcactg cataattctc ttactgtcat gccatccgta agatgctttt  4260
ctgtgactgg tgagtactca accaagtcat tctgagaata gtgtatgcgg cgaccgagtt  4320
gctcttgccc ggcgtcaata cgggataata ccgcgccaca tagcagaact ttaaaagtgc  4380
tcatcattgg aaaacgttct cggggcgaaa actctcaag gatcttaccg ctgttgagat  4440
ccagttcgat gtaacccact cgtgcaccca actgatcttc agcatctttt actttcacca  4500
gcgtttctgg gtgagcaaaa acaggaaggc aaaatgccgc aaaaaaggga ataagggcga  4560
cacgaaaatg ttgaatactc atactcttcc tttttcaata ttattgaagc atttatcagg  4620
gttattgtct catgagcgga tacatatttg aatgtattta gaaaaataaa caataggggg  4680
ttccgcgcac atttccccga aaagtgccac ctgacgtcta agaaaccatt attatcatga  4740
cattaaccta taaaaatagg cgtatcacga ggcccttcg tctcgcgcgt ttcggtgatg  4800
acggtgaaaa cctctgacac atgcagctcc cggagacggt cacagcttgt ctgtaagcgg  4860
atgccgggag cagacaagcc cgtcagggcg cgtcagcggg tgttgcggg tgtcggggct  4920
ggcttaacta tgcggcatca gagcagattg tactgagagt gcaccatatg cggtgtgaaa  4980
taccgcacag atgcgtaagg agaaaatacc gcatcaggcg ccattcgcca ttcaggctgc  5040
gcaactgttg ggaagggcga tcggtgcggg cctcttcgct attacgccag ctggcgaaag  5100
ggggatgtgc tgcaaggcga ttaagttggg taacgccagg gttttcccag tcacgacgtt  5160
gtaaaacgac ggccagtgcc acgctctccc ttatgcgact cctgcattag gaagcagccc  5220
agtagtaggt tgaggccgtt gagcaccgcc gccgcaagga atggtgcatg caaggagatg  5280
gcgcccaaca gtccccggc cacggggcct gccaccatac ccacgccgaa acaagcgctc  5340
atgagcccga agtggcgagc ccgatcttcc ccatccggtga tgtcggcgat ataggcgcca  5400
gcaaccgcac ctgtggcgcc ggtgatgccg gccacgatgc gtccggcgta gaggcgattt  5460
aaagacagga tatcagtggt ccaggctcta gttttgactc aacaatatca ccagctgaag  5520
cctatagagt acgagccata gataaaataa aagattttat ttagtctcca gaaaagggg  5580
ggaatgaaag accccacctg taggtttggc aagctagctt aagtaacgcc attttgcaag  5640
gcatggaaaa tacataactg agaatagaga agttcagatc aaggttagga acagagagac  5700
agcagaatat gggccaaaca ggatatctgt ggtaagcagt tcctgccccg gctcagggcc  5760
aagaacagat ggtccccaga tgcggtcccg ccctcagcag tttctagaga accatcagat  5820
gtttccaggg tgccccaagg acctgaaaat gaccctgtgc cttatttgaa ctaaccaatc  5880
agttcgcttc tcgcttctgt tcgcgcgctt ctgctcccg agctcaataa aagagcccac  5940
aaccccctcac tcggcgcgcc agtcctccga tagactgcgt cgcccgggta cccgtattcc  6000
caataaagcc tcttgctgtt tgcatccgaa tcgtggactg gctgatcctt gggagggtct  6060
cctcagattg attgactgcc cacctcgggg gtctttcatt tggaggttcc accgagattt  6120
ggagaccccg gcctagggac caccgacccc ccgccggga ggtaagctgg ccagcggtcg  6180
tttcgtgtct gtctctgtct ttgtgcgtgt ttgtgccggc atctaatgtt tgcgcctgcg  6240
tctgtactag ttagctaact agctctgtat ctggcggacc cgtggtgaa ctgacgagtt  6300
cggaacaccc ggccgcaacc ctgggagacg tcccagggac ttcgggggcc gtttttgtgg  6360
cccgacctga gtccaaaaat cccgatcgtt ttggactctt tggtgcaccc ccttagagg  6420
agggatatgt ggttctggta ggagacgaga acctaaaaca gttcccgcct ccgtctgaat  6480
ttttgctttc ggtttgggac cgaagccgcg ccgcgcgtct tgtctgctgc agcatcgttc  6540
tgtgttgtct ctgtctgact gtgtttctgt atttgtctga gaatatgggc ccgggctagc  6600
ctgttaccac tcccttaagt ttgacttag gtcactggaa agatgtcgag cggatcgctc  6660
acaaccagtc ggtagatgtc aagaagagac gttgggttac cttctgctct gcagaatgc  6720
caacctttaa cgtcggatgg ccgcgagacg gcacctttaa ccgagacctc atcacccagg  6780
ttaagatcaa ggtctttca cctggcccgc atggacaccc agaccaggtc ccctacatcg  6840
tgacctggga agccttggct tttgaccccc tccctgggt caagccctt gtacaccta  6900
agcctccgcc tcctcttcct ccatccgccc cgtctctccc ccttgaacct cctcgttcga  6960
ccccgctcg atcctccctt tatccagccc tcactcctc tctaggcgcc catatgagat  7020
catatgagat cttatatggg gcaccccgc ccttgtaaa cttccctgac cctgacatga  7080
caagagttac taacagccc tctctccaag ctcacttaca ggctctctac ttagtccagc  7140
acgaagtctg gagacctctg gcggcagcct accaagaaca actggaccga ccggtggtac  7200
ctcaccctta ccgagtcggc gacacagtgt gggtccgccg acaccagact aagaacctag  7260
aacctcgctg gaaaggacct tacacagtcc tgctgaccac ccccaccgcc ctcaaagtag  7320
acggcatcgc agcttggata cacgccgccc acgtgaaggc tgccgacccc gggggtggac  7380
catcctctag accg                                                    7394

SEQ ID NO: 22          moltype = DNA   length = 18
FEATURE                Location/Qualifiers
source                 1..18
                       mol_type = genomic DNA
                       organism = Mus musculus
SEQUENCE: 22
gacccctaaca gttattac                                               18
```

| | | |
|---|---|---|
| SEQ ID NO: 23 | moltype = DNA length = 21 | |
| FEATURE | Location/Qualifiers | |
| source | 1..21<br>mol_type = genomic DNA<br>organism = Mus musculus | |
| SEQUENCE: 23 | | |
| gttttctcaa gtacggaaat a | | 21 |
| | | |
| SEQ ID NO: 24 | moltype = DNA length = 33 | |
| FEATURE | Location/Qualifiers | |
| source | 1..33<br>mol_type = genomic DNA<br>organism = Mus musculus | |
| SEQUENCE: 24 | | |
| gcagtcagtt cttctggcag ctggcaactc atc | | 33 |
| | | |
| SEQ ID NO: 25 | moltype = DNA length = 15 | |
| FEATURE | Location/Qualifiers | |
| source | 1..15<br>mol_type = genomic DNA<br>organism = Mus musculus | |
| SEQUENCE: 25 | | |
| aagggacatc cagtt | | 15 |
| | | |
| SEQ ID NO: 26 | moltype = DNA length = 18 | |
| FEATURE | Location/Qualifiers | |
| source | 1..18<br>mol_type = genomic DNA<br>organism = Mus musculus | |
| SEQUENCE: 26 | | |
| tttcagaatc aagaagtt | | 18 |
| | | |
| SEQ ID NO: 27 | moltype = DNA length = 33 | |
| FEATURE | Location/Qualifiers | |
| source | 1..33<br>mol_type = genomic DNA<br>organism = Mus musculus | |
| SEQUENCE: 27 | | |
| gccagcctgg ggggaagcca agacacccag tac | | 33 |
| | | |
| SEQ ID NO: 28 | moltype = AA length = 27 | |
| FEATURE | Location/Qualifiers | |
| REGION | 1..27<br>note = Synthetic | |
| source | 1..27<br>mol_type = protein<br>organism = synthetic construct | |
| SEQUENCE: 28 | | |
| RAKRSGSGAT NFSLLKQAGD VEENPGP | | 27 |
| | | |
| SEQ ID NO: 29 | moltype = AA length = 9 | |
| FEATURE | Location/Qualifiers | |
| source | 1..9<br>mol_type = protein<br>organism = Homo sapiens | |
| SEQUENCE: 29 | | |
| TLLASICWV | | 9 |
| | | |
| SEQ ID NO: 30 | moltype = AA length = 9 | |
| FEATURE | Location/Qualifiers | |
| source | 1..9<br>mol_type = protein<br>organism = Homo sapiens | |
| SEQUENCE: 30 | | |
| ELPEFLLFL | | 9 |
| | | |
| SEQ ID NO: 31 | moltype = AA length = 9 | |
| FEATURE | Location/Qualifiers | |
| source | 1..9<br>mol_type = protein<br>organism = Homo sapiens | |
| SEQUENCE: 31 | | |
| ALVLEIFTL | | 9 |
| | | |
| SEQ ID NO: 32 | moltype = AA length = 9 | |
| FEATURE | Location/Qualifiers | |
| source | 1..9<br>mol_type = protein | |

```
                          organism = Homo sapiens
SEQUENCE: 32
ILQRRFLAV                                                                       9

SEQ ID NO: 33             moltype = AA  length = 9
FEATURE                   Location/Qualifiers
source                    1..9
                          mol_type = protein
                          organism = Homo sapiens
SEQUENCE: 33
ALLRSGPYM                                                                       9

SEQ ID NO: 34             moltype = AA  length = 8
FEATURE                   Location/Qualifiers
source                    1..8
                          mol_type = protein
                          organism = Homo sapiens
SEQUENCE: 34
LVEIFTLL                                                                        8

SEQ ID NO: 35             moltype = AA  length = 9
FEATURE                   Location/Qualifiers
source                    1..9
                          mol_type = protein
                          organism = Homo sapiens
SEQUENCE: 35
VQQVQCWCV                                                                       9

SEQ ID NO: 36             moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 36
ggctactttc agcaggagga                                                          20

SEQ ID NO: 37             moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 37
aggcctctgc actgatgttc                                                          20

SEQ ID NO: 38             moltype = DNA  length = 41
FEATURE                   Location/Qualifiers
misc_feature              1..41
                          note = Synthetic
source                    1..41
                          mol_type = other DNA
                          organism = synthetic construct
SEQUENCE: 38
ccatcctcta gaccgccatg aagacagtga ctggaccttt g                                  41

SEQ ID NO: 39             moltype = DNA  length = 50
FEATURE                   Location/Qualifiers
misc_feature              1..50
                          note = Synthetic
source                    1..50
                          mol_type = other DNA
                          organism = synthetic construct
SEQUENCE: 39
tggtggctcc ggatccggac cgcttggccc gactggacca cagcctcagc                         50

SEQ ID NO: 40             moltype = DNA  length = 51
FEATURE                   Location/Qualifiers
misc_feature              1..51
                          note = Synthetic
source                    1..51
                          mol_type = other DNA
                          organism = synthetic construct
SEQUENCE: 40
gtaccgtcga ctgcagaatt cggtcaggaa ttttttttct tgaccatggc c                       51

SEQ ID NO: 41             moltype = DNA  length = 51
```

```
FEATURE                     Location/Qualifiers
misc_feature                1..51
                            note = Synthetic
source                      1..51
                            mol_type = other DNA
                            organism = synthetic construct
SEQUENCE: 41
gggccaagcg gtccggatcc ggagccacca acttcagcct gctgaagcag g          51

SEQ ID NO: 42               moltype = DNA  length = 52
FEATURE                     Location/Qualifiers
misc_feature                1..52
                            note = Synthetic
source                      1..52
                            mol_type = other DNA
                            organism = synthetic construct
SEQUENCE: 42
accaacttca gcctgctgaa gcaggccggc gacgtggagg agaaccccgg cc         52

SEQ ID NO: 43               moltype = DNA  length = 44
FEATURE                     Location/Qualifiers
misc_feature                1..44
                            note = Synthetic
source                      1..44
                            mol_type = other DNA
                            organism = synthetic construct
SEQUENCE: 43
tggaggagaa ccccggcccc atggctacaa ggctcctctg ttac                  44

SEQ ID NO: 44               moltype = AA  length = 6
FEATURE                     Location/Qualifiers
source                      1..6
                            mol_type = protein
                            organism = Homo sapiens
SEQUENCE: 44
NSASQS                                                            6

SEQ ID NO: 45               moltype = AA  length = 6
FEATURE                     Location/Qualifiers
source                      1..6
                            mol_type = protein
                            organism = Homo sapiens
SEQUENCE: 45
VYSSGN                                                            6

SEQ ID NO: 46               moltype = AA  length = 11
FEATURE                     Location/Qualifiers
source                      1..11
                            mol_type = protein
                            organism = Homo sapiens
SEQUENCE: 46
VVHSSNTGKL I                                                      11

SEQ ID NO: 47               moltype = AA  length = 5
FEATURE                     Location/Qualifiers
source                      1..5
                            mol_type = protein
                            organism = Homo sapiens
SEQUENCE: 47
MNHEY                                                             5

SEQ ID NO: 48               moltype = AA  length = 6
FEATURE                     Location/Qualifiers
source                      1..6
                            mol_type = protein
                            organism = Homo sapiens
SEQUENCE: 48
SVGAGI                                                            6

SEQ ID NO: 49               moltype = AA  length = 18
FEATURE                     Location/Qualifiers
source                      1..18
                            mol_type = protein
                            organism = Homo sapiens
SEQUENCE: 49
ASSYSLTSGG ALVSYEQY                                               18

SEQ ID NO: 50               moltype = AA  length = 121
FEATURE                     Location/Qualifiers
```

| source | 1..121
mol_type = protein
organism = Homo sapiens |

SEQUENCE: 50

```
MISLRVLLVI LWLQLSWVWS QRKEVEQDPG PFNVPEGATV AFNCTYSNSA SQSFFWYRQD   60
CRKEPKLLMS VYSSGNEDGR FTAQLNRASQ YISLLIRDSK LSDSATYLCV VHSSNTGKLI  120
F                                                                 121
```

| SEQ ID NO: 51 | moltype = AA  length = 129 |
|---|---|
| FEATURE | Location/Qualifiers |
| source | 1..129
mol_type = protein
organism = Homo sapiens |

SEQUENCE: 51

```
MSIGLLCCAA LSLLWAGPVN AGVTQTPKFQ VLKTGQSMTL QCAQDMNHEY MSWYRQDPGM   60
GLRLIHYSVG AGITDQGEVP NGYNVSRSTT EDFPLRLLSA APSQTSVYFC ASSYSLTSGG  120
ALVSYEQYF                                                         129
```

| SEQ ID NO: 52 | moltype = AA  length = 159 |
|---|---|
| FEATURE | Location/Qualifiers |
| source | 1..159
mol_type = protein
organism = Homo sapiens |

SEQUENCE: 52

```
GQGTTLQVKP DIQNPDPAVY QLRDSKSSDK SVCLFTDFDS QTNVSQSKDS DVYITDKTVL   60
DMRSMDFKSN SAVAWSNKSD FACANAFNNS IIPEDTFFPS PESSCDVKLV EKSFETDTNL  120
NFQNLSVIGF RILLLKVAGF NLLMTLRLWS SRAKRSGSG                         159
```

| SEQ ID NO: 53 | moltype = AA  length = 188 |
|---|---|
| FEATURE | Location/Qualifiers |
| source | 1..188
mol_type = protein
organism = Homo sapiens |

SEQUENCE: 53

```
GPGTRLTVTE DLKNVFPPEV AVFEPSEAEI SHTQKATLVC LATGFYPDHV ELSWWVNGKE   60
VHSGVSTDPQ PLKEQPALND SRYCLSSRLR VSATFWQNPR NHFRCQVQFY GLSENDEWTQ  120
DRAKPVTQIV SAEAWGRADC GFTSESYQQG VLSATILYEI LLGKATLYAV LVSALVLMAM  180
VKRKDSRG                                                          188
```

| SEQ ID NO: 54 | moltype = AA  length = 280 |
|---|---|
| FEATURE | Location/Qualifiers |
| source | 1..280
mol_type = protein
organism = Homo sapiens |

SEQUENCE: 54

```
MISLRVLLVI LWLQLSWVWS QRKEVEQDPG PFNVPEGATV AFNCTYSNSA SQSFFWYRQD   60
CRKEPKLLMS VYSSGNEDGR FTAQLNRASQ YISLLIRDSK LSDSATYLCV VHSSNTGKLI  120
FGQGTTLQVK PDIQNPDPAV YQLRDSKSSD KSVCLFTDFD SQTNVSQSKD SDVYITDKTV  180
LDMRSMDFKS NSAVAWSNKS DFACANAFNN SIIPEDTFFP SPESSCDVKL VEKSFETDTN  240
LNFQNLSVIG FRILLLKVAG FNLLMTLRLW SSRAKRSGSG                        280
```

| SEQ ID NO: 55 | moltype = AA  length = 317 |
|---|---|
| FEATURE | Location/Qualifiers |
| source | 1..317
mol_type = protein
organism = Homo sapiens |

SEQUENCE: 55

```
MSIGLLCCAA LSLLWAGPVN AGVTQTPKFQ VLKTGQSMTL QCAQDMNHEY MSWYRQDPGM   60
GLRLIHYSVG AGITDQGEVP NGYNVSRSTT EDFPLRLLSA APSQTSVYFC ASSYSLTSGG  120
ALVSYEQYFG PGTRLTVTED LKNVFPPEVA VFEPSEAEIS HTQKATLVCL ATGFYPDHVE  180
LSWWVNGKEV HSGVSTDPQP LKEQPALNDS RYCLSSRLRV SATFWQNPRN HFRCQVQFYG  240
LSENDEWTQD RAKPVTQIVS AEAWGRADCG FTSESYQQGV LSATILYEIL LGKATLYAVL  300
VSALVLMAMV KRKDSRG                                                317
```

| SEQ ID NO: 56 | moltype = DNA  length = 843 |
|---|---|
| FEATURE | Location/Qualifiers |
| source | 1..843
mol_type = genomic DNA
organism = Homo sapiens |

SEQUENCE: 56

```
atgatatcct tgagagtttt actggtgatc ctgtggcttc agttaagctg ggtttggagc   60
caacggaagg aggtggagca ggatcctgga cccttcaatg ttccagaggg agccactgtc  120
gctttcaact gtacttacag caacagtgct tctcagtctt tcttctggta cagacaggat  180
tgcaggaaag aacctaagtt gctgatgtcc gtatactcca gtggtaatga agatggaagg  240
tttacagcac agctcaatag agccagccag tatatttccc tgctcatcag agactccaag  300
ctcagtgatt cagccaccta cctctgtgtg gtccactcta gcaacacagg caaactaatc  360
tttgggcaag gcacaacttt acaagtaaaa ccagatatcc agaaccctga ccctgccgtg  420
taccagctga gagactctaa atccagtgac aagtctgtct gcctattcac cgattttgat  480
tctcaaaaca atgtgtcaca aagtaaggat tctgatgtgt atatcacaga caaaactgtg  540
```

```
ctagacatga ggtctatgga cttcaagagc aacagtgctg tggcctggag caacaaatct    600
gactttgcat gtgcaaacgc cttcaacaac agcattattc cagaagacac cttcttcccc    660
agcccagaaa gttcctgtga tgtcaagctg gtcgagaaaa gctttgaaac agatacgaac    720
ctaaactttc aaaacctgtc agtgattggg ttccgaatcc tcctcctgaa agtggccggg    780
tttaatctgc tcatgacgct gcggctgtgg tccagccggg ccaagcggtc cggatccgga    840
tga                                                                  843

SEQ ID NO: 57          moltype = DNA  length = 954
FEATURE                Location/Qualifiers
source                 1..954
                       mol_type = genomic DNA
                       organism = Homo sapiens
SEQUENCE: 57
atgagcatcg gcctcctgtg ctgtgcagcc ttgtctctcc tgtgggcagg tccagtgaat     60
gctggtgtca ctcagacccc aaaattccag gtcctgaaga caggacagag catgacactg    120
cagtgtgccc aggatatgaa ccatgaatac atgtcctggt atcgacaaga cccaggcatg    180
gggctgaggc tgattcatta ctcagttggt gctggtatca ctgaccaagg agaagtcccc    240
aatggctaca atgtctccag atcaaccaca gaggatttcc cgctcaggct gctgtcggct    300
gctccctccc agacatctgt gtacttctgt gccagcagtt actctttgac tagcggggg    360
gccttagtct cctacgagca gtacttcggg ccgggcacca ggctcacggt cacagaggac    420
ctgaaaaacg tgttcccacc cgaggtcgct gtgtttgagc catcagaagc agagatctcc    480
cacacccaaa aggccacact ggtatgcctg gccacaggct tctacccga ccacgtggag    540
ctgagctggt gggtgaatgg gaaggaggtg cacagtgggg tcagcacaga cccgcagccc    600
ctcaaggagc agcccgccct caatgactcc agatactgcc tgagcagccg cctgagggtc    660
tcggccacct tctggcagaa cccccgcaac cacttccgct gtcaagtcca gttctacggg    720
ctctcggaga atgacgagtg gacccaggat agggccaaac ccgtcaccga gatcgtcagc    780
gccgaggcct ggggtagagc agactgtggc ttcacctccg agtcttacca gcaagggtc    840
ctgtctgcca ccatcctcta tgagatcttg ctagggaagg ccaccttgta tgccgtgctg    900
gtcagtgccc tcgtgctgat ggctatggtc aagagaaagg attccagagg ctag          954

SEQ ID NO: 58          moltype = AA  length = 9
FEATURE                Location/Qualifiers
source                 1..9
                       mol_type = protein
                       organism = Homo sapiens
SEQUENCE: 58
LVLEIFTLL                                                              9
```

The invention claimed is:

1. A pharmaceutical composition comprising (a) an isolated host cell, wherein the host cell comprises a recombinant expression vector, wherein the recombinant expression vector comprises a nucleic acid, wherein the nucleic acid comprises a nucleotide sequence encoding a T cell receptor (TCR) having antigenic specificity for human thyroglobulin (TG), wherein the TCR comprises an α chain complementarity determining region (CDR) 1 comprising the amino acid sequence of SEQ ID NO: 3, an α chain CDR2 comprising the amino acid sequence of SEQ ID NO: 4, an α chain CDR3 comprising the amino acid sequence of SEQ ID NO: 5, a β chain CDR1 comprising the amino acid sequence of SEQ ID NO: 6, a β chain CDR2 comprising the amino acid sequence of SEQ ID NO: 7, and a β chain CDR3 comprising the amino acid sequence of SEQ ID NO: 8, and (b) a pharmaceutically acceptable carrier.

2. The pharmaceutical composition of claim 1, wherein the TCR comprises an α chain variable region comprising the amino acid sequence of SEQ ID NO: 9 and a β chain variable region comprising the amino acid sequence of SEQ ID NO: 10.

3. The pharmaceutical composition of claim 1, wherein the TCR further comprises an α chain constant region comprising the amino acid sequence of SEQ ID NO: 13 and a β chain constant region comprising the amino acid sequence of SEQ ID NO: 14.

4. The pharmaceutical composition of claim 1, wherein the TCR comprises an α chain comprising the amino acid sequence of SEQ ID NO: 11 and a β chain comprising the amino acid sequence of SEQ ID NO: 12.

5. The pharmaceutical composition of claim 1, wherein the nucleotide sequence comprises SEQ ID NOs: 22-27.

6. The pharmaceutical composition of claim 1, wherein the nucleotide sequence comprises SEQ ID NOs: 15 and 16.

7. The pharmaceutical composition of claim 1, wherein the nucleotide sequence comprises SEQ ID NOs: 19 and 20.

8. The pharmaceutical composition of claim 1, wherein the nucleotide sequence comprises SEQ ID NOs: 17 and 18.

9. The pharmaceutical composition of claim 1, wherein the nucleotide sequence comprises SEQ ID NO: 21.

10. A pharmaceutical composition comprising (a) an isolated host cell, wherein the host cell comprises a recombinant expression vector, wherein the recombinant expression vector comprises a nucleic acid, wherein the nucleic acid comprises a nucleotide sequence encoding a polypeptide comprising a functional portion of a T cell receptor (TCR) having antigenic specificity for human thyroglobulin (TG), wherein the TCR comprises an α chain complementarity determining region (CDR) 1 comprising the amino acid sequence of SEQ ID NO: 3, an α chain CDR2 comprising the amino acid sequence of SEQ ID NO: 4, an α chain CDR3 comprising the amino acid sequence of SEQ ID NO: 5, a β chain CDR1 comprising the amino acid sequence of SEQ ID NO: 6, a β chain CDR2 comprising the amino acid sequence of SEQ ID NO: 7, and a β chain CDR3 comprising the amino acid sequence of SEQ ID NO: 8, wherein the functional portion comprises the amino acid sequences of SEQ ID NOs: 3-8, and (b) a pharmaceutically acceptable carrier.

11. The pharmaceutical composition of claim 10, wherein the functional portion comprises the amino acid sequence of both SEQ ID NOs: 9 and 10.

12. The pharmaceutical composition of claim 10, wherein the functional portion comprises the amino acid sequence of both SEQ ID NOs: 11 and 12.

13. The pharmaceutical composition of claim 10, wherein the polypeptide comprises a self-cleaving, viral linker peptide.

14. A pharmaceutical composition comprising (a) an isolated host cell, wherein the host cell comprises a recombinant expression vector, wherein the recombinant expression vector comprises a nucleic acid, wherein the nucleic acid comprises a nucleotide sequence encoding a protein having antigenic specificity for human thyroglobulin (TG), wherein the protein comprises a T cell receptor (TCR) α chain complementarity determining region (CDR) 1 comprising the amino acid sequence of SEQ ID NO: 3, a TCR α chain CDR2 comprising the amino acid sequence of SEQ ID NO: 4, a TCR α chain CDR3 comprising the amino acid sequence of SEQ ID NO: 5, a TCR β chain CDR1 comprising the amino acid sequence of SEQ ID NO: 6, a TCR β chain CDR2 comprising the amino acid sequence of SEQ ID NO: 7, and a TCR β chain CDR3 comprising the amino acid sequence of SEQ ID NO: 8, wherein the protein comprises a first polypeptide chain comprising the amino acid sequences of SEQ ID NOs: 3-5 and a second polypeptide chain comprising the amino acid sequences of SEQ ID NOs: 6-8, and (b) a pharmaceutically acceptable carrier.

15. The pharmaceutical composition of claim 14, wherein the first polypeptide chain comprises the amino acid sequence of SEQ ID NO: 9 and the second polypeptide chain comprising the amino acid sequence of SEQ ID NO: 10.

16. The pharmaceutical composition of claim 14, wherein the first polypeptide chain comprises the amino acid sequence of SEQ ID NO: 11 and the second polypeptide chain comprises the amino acid sequence of SEQ ID NO: 12.

17. The pharmaceutical composition of claim 1, comprising a population of cells comprising at least one of the host cell.

18. The pharmaceutical composition of claim 10, comprising a population of cells comprising at least one of the host cell.

19. The pharmaceutical composition of claim 14, comprising a population of cells comprising at least one of the host cell.

* * * * *